United States Patent
Nguyen et al.

(10) Patent No.: US 10,896,741 B2
(45) Date of Patent: Jan. 19, 2021

(54) PREDICTION OF PHENOTYPES USING RECOMMENDER SYSTEMS

(71) Applicant: Ancestry.com DNA, LLC, Lehi, UT (US)

(72) Inventors: Thi Hong Luong Nguyen, San Bruno, CA (US); Natalie Telis, Mountain View, CA (US); Marie-Virginie Coignet, Oakland, CA (US)

(73) Assignee: Ancestry.com DNA, LLC, Lehi, UT (US)

( * ) Notice: Subject to any disclaimer, the term of this patent is extended or adjusted under 35 U.S.C. 154(b) by 0 days.

(21) Appl. No.: 16/543,033

(22) Filed: Aug. 16, 2019

(65) Prior Publication Data
US 2020/0058368 A1 Feb. 20, 2020

Related U.S. Application Data

(60) Provisional application No. 62/719,553, filed on Aug. 17, 2018, provisional application No. 62/752,523, (Continued)

(51) Int. Cl.
*G16B 20/00* (2019.01)
*G06N 5/02* (2006.01)
(Continued)

(52) U.S. Cl.
CPC ............... *G16B 20/00* (2019.02); *G06N 5/02* (2013.01); *G06N 5/04* (2013.01); *G06N 20/00* (2019.01); *G16H 10/20* (2018.01)

(58) Field of Classification Search
CPC . G06N 20/00; G06N 5/02; G06N 5/04; G16B 20/00; G16B 10/00; G16B 40/20; G16B 40/30; G16H 10/20; G16H 50/70
See application file for complete search history.

(56) References Cited

U.S. PATENT DOCUMENTS

| | | |
|---|---|---|
| 9,910,962 B1 | 3/2018 | Fakhrai-Rad et al. |
| 10,114,922 B2 | 10/2018 | Byrnes et al. |

(Continued)

FOREIGN PATENT DOCUMENTS

CN 106846029 A 6/2017

OTHER PUBLICATIONS

Joshi et al., "Identifiable Phenotyping using Constrained Non-Negative Matrix Factorization", 2016, Proceedings of Machine Learning for Healthcare 2016, JMLR W&C Track vol. 56, pp. 1-24 (Year: 2016).*

(Continued)

*Primary Examiner* — Kamran Afshar
*Assistant Examiner* — Brent Johnston Hoover
(74) *Attorney, Agent, or Firm* — Fenwick & West LLP

(57) ABSTRACT

A computing server may use one or more recommender systems to predict phenotypes of individuals based on survey responses, other phenotypes, environmental factors, and genetic data of the individuals. The computing server may retrieve survey responses of a set of individuals regarding a set of phenotypes of the individuals. The computing server may construct a matrix that includes the values of the phenotypes. The computing server may predict an undetermined phenotype of a target individual using collaborative filtering, which provides the prediction based on other phenotypes of the target individuals and based on at least another individual's phenotypes. The computing server may also predict a target phenotype based on the phenotype of other individuals who are similar to the target individual. The computing server may determine another individual is similar to the target individual based on the length of identity-by-descent (IBD) segments between the two individuals.

19 Claims, 11 Drawing Sheets

Related U.S. Application Data filed on Oct. 30, 2018, provisional application No. 62/857,691, filed on Jun. 5, 2019.

(51) Int. Cl.
*G16H 10/20* (2018.01)
*G06N 20/00* (2019.01)
*G06N 5/04* (2006.01)

(56) References Cited

U.S. PATENT DOCUMENTS

| | | | |
|---|---|---|---|
| 10,223,498 B2 | 3/2019 | Han et al. | |
| 2002/0156596 A1* | 10/2002 | Caruso | G06Q 30/02 |
| | | | 702/179 |
| 2004/0267458 A1 | 12/2004 | Judson et al. | |
| 2008/0228043 A1 | 9/2008 | Kenedy et al. | |
| 2010/0256917 A1 | 10/2010 | McVean et al. | |
| 2014/0067355 A1 | 3/2014 | Noto et al. | |
| 2014/0194300 A1 | 7/2014 | Song et al. | |
| 2015/0106115 A1* | 4/2015 | Hu | G06F 19/00 |
| | | | 705/3 |
| 2017/0017752 A1 | 1/2017 | Noto et al. | |
| 2017/0220738 A1 | 8/2017 | Barber et al. | |
| 2018/0329033 A1 | 11/2018 | Pratt et al. | |
| 2018/0330824 A1* | 11/2018 | Athey | G16H 10/60 |

OTHER PUBLICATIONS

Braak et al., "Identity-by-Descent Matrix Decomposition Using Latent Ancestral Allele Models", Jul. 1, 2010, Genetics, vol. 185 No. 3, pp. 1045-1057 (Year: 2010).*

Li et al., "Towards Unsupervised Gene Selection: A Matrix Factorization Framework", Jun. 2017, IEEE/ACM Transactions on Computational Biology and Bioinformatics, vol. 14, No. 3, pp. 514-521 (Year: 2017).*

Bastian, M. et al., "Gephi: an open source software for exploring and manipulating networks," Third international AAAI conference on weblogs and social media, 2009, 361-362.

Han, E. et al., "Clustering of 770,000 genomes reveals post-colonial population structure of North America," Nature communications, 2017, vol. 8, pp. 1-12.

Hug, N., "Surprise, a Python library for recommender systems," 2017, 5 pages, [Online] [Retrieved Sep. 25, 2019], Retrieved from the internet <URL: http://surpriselib.com/>.

Itan, Y. et al., "The origins of lactase persistence in Europe," PLoS computational biology, 2009, vol. 5, No. 8, pp. 1-13.

Ke, X. et al. "Singleton SNPs in the human genome and implications for genome-wide association studies," European Journal of Human Genetics, 2008, vol. 16, No. 4, 10 pages.

Ranciaro, A. et al., "Genetic origins of lactase persistence and the spread of pastoralism in Africa," The American Journal of Human Genetics, 2014, vol. 94, No. 4, pp. 496-510.

Roach, J.C. et al., "Analysis of genetic inheritance in a family quartet by whole-genome sequencing," Science, 2010, vol. 328, No. 5978, pp. 636-639.

Sturm, R.A. et al., "A single SNP in an evolutionary conserved region within intron 86 of the HERC2 gene determines human blue-brown eye color," The American Journal of Human Genetics, 2008, vol. 82, No. 2, pp. 424-431.

The 1000 Genomes Project Consortium, "A global reference for human genetic variation," Macmillan Publishers Limited, Nature, Oct. 1 2015, vol. 526, No. 7571, pp. 68-74.

Montesinos-Lopez, A. A. et al., 'Prediction of multiple-trait and multipleenvironment genomic data using recommender systems', G3: Genes, Genomes, Genetics, Jan. 2018, vol. 8, pp. 131-147.

PCT International Search Report and Written Opinion, PCT Application No. PCT/IB2019/056939, dated Jan. 3, 2020, 11 pages.

PCT International Search Report and Written Opinion, PCT Application No. PCT/IB2019/057667, dated Jan. 10, 2020, 10 pages.

Zeng, X. et al., 'Probability-based collaborative filtering model for predicting gene-disease associations', BMC Medical Genomics, 2017, vol. 10, No. 76, pp. 45-53.

* cited by examiner

PREDICTION OF PHENOTYPES USING RECOMMENDER SYSTEMS

CROSS-REFERENCE TO RELATED APPLICATIONS

The present application claims the benefit of U.S. Provisional Patent Application Nos. 62/719,553 filed on Aug. 17, 2018, 62/752,523 filed on Oct. 30, 2018, and 62/857,691 filed on Jun. 5, 2019, which are all hereby incorporated by reference in their entirety.

BACKGROUND

Embodiments relate to predicting phenotypes of an individual using a recommender system and, more specifically, predicting phenotypes based on genetic data and survey responses of a target and other individuals who are similar to the target.

Although humans are, genetically speaking, almost entirely identical, small differences in human DNA are responsible for some observed variations between individuals. The variations among individuals can be manifested by different expressions of phenotypes, which may pertain to certain traits and characteristics of individuals, such as hair color, eye color, the susceptibility of certain diseases, etc. While an individual's expression of a phenotype is often related to the individual's DNA sequences, the exact relationship is often not immediately apparent to researchers. For example, the exact gene loci or sequence that will lead to a certain phenotype is still unknown for many phenotypes. Also, the expression of a phenotype is often based on multiple genes. The polygenic nature of a phenotype often impacts the predictability of expression.

Hence, the prediction of traits and characteristics of an individual has been difficult. It is particularly so for phenotypes that may also be affected by other non-genetic factors such as environmental factors. For example, some traits such as weight and height are both affected by the genes of the individual and the developmental environment and experiences of the individual. Accurate predictions of phenotypes have been challenging in the study of biology and genetics.

SUMMARY

Systems and methods that predict a phenotype of a target individual based on other phenotypes of the target individual and data of other individuals using recommender systems such as collaborative filtering are disclosed. The prediction may be based on individuals who are similar to the target individual as reflected, for example, in genetic data of the individuals.

In one embodiment, a computer-implemented method is described. The method may include retrieving survey responses of a set of individuals. The survey response are related to a set of phenotypes of the individuals. The set of individuals includes one or more target individuals. The method also may include constructing a matrix that arranges the set of individuals in a first dimension of the matrix and the set of phenotypes in a second dimension of the matrix. At least a subset of elements in the matrix correspond to numerical representations of the individuals' phenotypes obtained from the survey responses. The method further may include identifying an undetermined phenotype of a target individual. The matrix may not have a value at the particular element corresponding to the undetermined phenotype of the target individual. The method further may include determining a prediction of the undetermined phenotype of the target individual by collaborative filtering. The collaborative filtering may be based on other phenotypes of the target individual and based on at least another individual's phenotypes as represented in numerical representations in the matrix. One or more phenotypes of more than one target individuals may be determined.

In another embodiment, another computer-implemented method is described. The method may include retrieving user data of a set of individuals. The set of individuals includes one or more target individuals. The use data may include a genetic dataset and a phenotype dataset. The method also may include converting a subset of values of the user data into a set of feature vectors. A feature vector may correspond to an individual and may include one or more numerical representations of the genetic data of the individual and one or more numerical representations of the phenotype data of the individual. The method further may include classifying the set of feature vectors into a plurality of clusters. Each cluster includes one or more feature vectors representing one or more individuals. The method further may include identifying one or more similar individuals who are similar to the target individual. The similar individuals may belong to one of the clusters to which the target individual belongs. The method further may include predicting a value of a phenotype of the target individual based on values of the phenotype of the similar individuals. The method may also predict or adjust the value of the phenotype based on correlation of the target phenotype with other phenotypes.

In yet another embodiment, a non-transitory computer readable medium that is configured to store instructions is described. The instructions, when executed by one or more processors, cause the one or more processors to perform a process that includes steps described in the above computer-implemented methods or described in any embodiments of this disclosure. In yet another embodiment, a system may include one or more processors and a storage medium that is configured to store instructions. The instructions, when executed by one or more processors, cause the one or more processors to perform a process that includes steps described in the above computer-implemented methods or described in any embodiments of this disclosure.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Example System Environment

Figure 1:
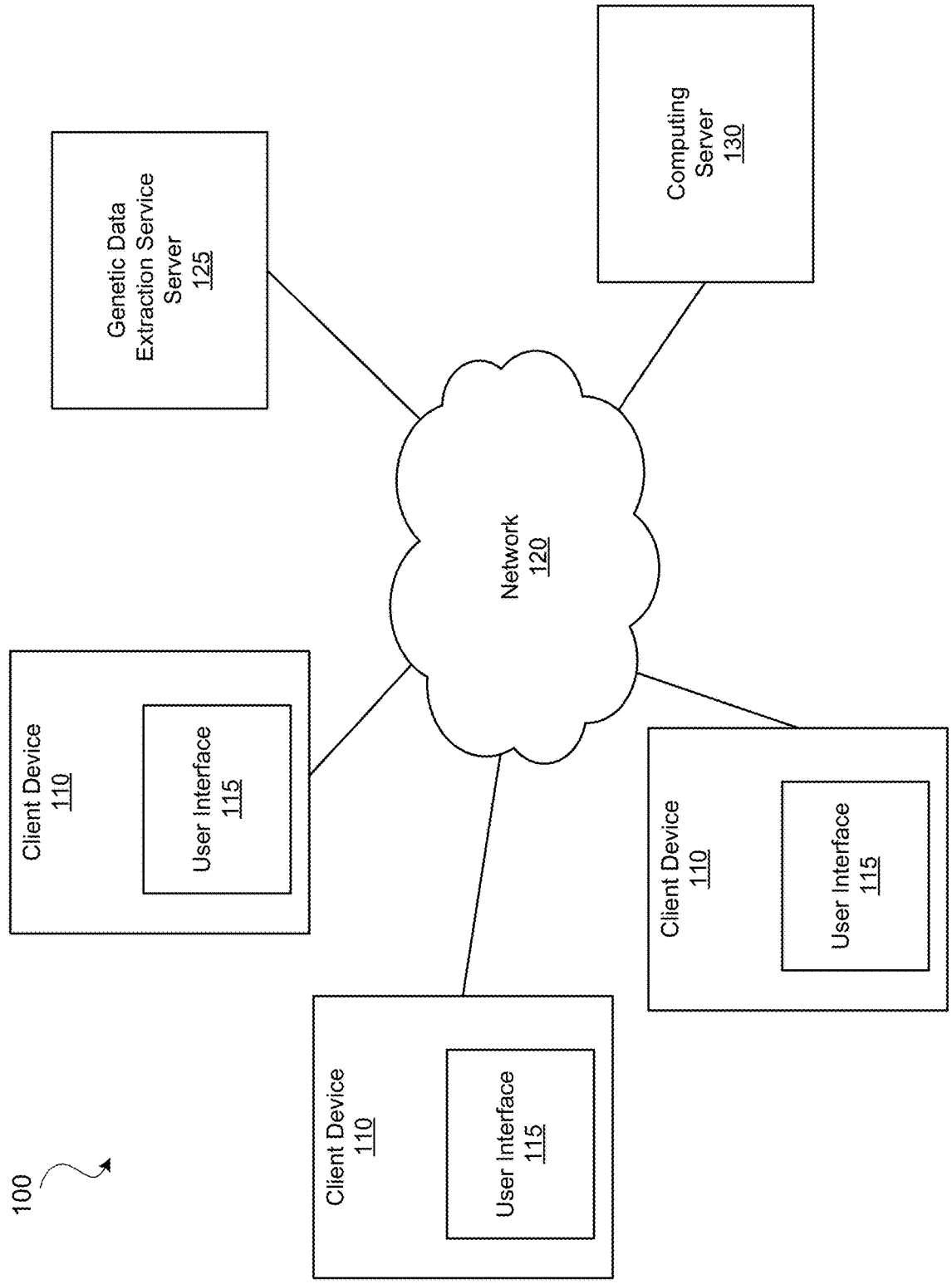
FIG. 1 is a block diagram of a system environment of an example computing system, in accordance with an embodiment.

FIG. 1 illustrates a diagram of a system environment 100 of an example computing server 130, in accordance with an embodiment. The system environment 100 shown in FIG. 1 includes one or more client devices 110, a network 120, a genetic data extraction service server 125, and a computing server 130. In various embodiments, the system environment 100 may include fewer or additional components. The system environment 100 may also include different components.

The client devices 110 are one or more computing devices capable of receiving user input as well as transmitting and/or receiving data via a network 120. Example computing devices include desktop computers, laptop computers, personal digital assistants (PDAs), smartphones, tablets, wearable electronic devices (e.g., smartwatches), smart household appliance (e.g., smart televisions, smart speakers, smart home hubs), Internet of Things (IoT) devices or other suitable electronic devices. A client device 110 communicates to other components via the network 120. Users may be customers of the computing server 130 or any individuals who access the system of the computing server 130, such as an online website or a mobile application. In one embodiment, a client device 110 executes an application that launches a graphical user interface (GUI) for a user of the client device 110 to interact with the computing server 130. The GUI may be an example of a user interface 115. A client device 110 may also execute a web browser application to enable interactions between the client device 110 and the computing server 130 via the network 120. In another embodiment, the user interface 115 may take the form of a software application published by the computing server 130 and installed on the user device 110. In yet another embodiment, a client device 110 interacts with the computing server 130 through an application programming interface (API) running on a native operating system of the client device 110, such as IOS or ANDROID.

The network 120 provides connections to the components of the system environment 100 through one or more sub-networks, which may include any combination of local area and/or wide area networks, using both wired and/or wireless communication systems. In one embodiment, a network 120 uses standard communications technologies and/or protocols. For example, a network 120 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 120 may be represented using any suitable format, such as hypertext markup language (HTML) or extensible markup language (XML). In some embodiments, all or some of the communication links of a network 120 may be encrypted using any suitable technique or techniques such as secure sockets layer (SSL), transport layer security (TLS), virtual private networks (VPNs), Internet Protocol security (IPsec), etc. The network 120 also includes links and packet switching networks such as the Internet.

Individuals, who may be customers of a company operating the computing server 130, provide biological samples for analysis of their genetic data. In one embodiment, an individual uses a sample collection kit to provide a biological sample (e.g., saliva, blood, hair, tissue) from which genetic data is extracted and determined according to nucleotide processing techniques such as amplification and sequencing. Amplification may include using polymerase chain reaction (PCR) to amplify segments of nucleotide samples. Sequencing may include sequencing of deoxyribonucleic acid (DNA) sequencing, ribonucleic acid (RNA) sequencing, etc. Suitable sequencing techniques may include Sanger sequencing and massively parallel sequencing such as various next-generation sequencing (NGS) techniques including whole genome sequencing, pyrosequencing, sequencing by synthesis, sequencing by ligation, and ion semiconductor sequencing. Genetic data extraction service server 125 receives biological samples from users of the computing server 130. The genetic data extraction service server 125 performs sequencing of the biological samples and determines the base pair sequences of the individuals. The genetic data extraction service server 125 generates the genetic data of the individuals based on the sequencing results. The genetic data may include data sequenced from DNA or RNA and may include base pairs from coding and/or noncoding regions of DNA.

The genetic data may take different forms. For example, in one embodiment, the genetic data may be the base pair sequence of an individual. The base pair sequence may include the whole genome or a part of the genome such as certain genetic loci of interest. In another embodiment, the genetic data extraction service server 125 may determine genotypes from sequencing results, for example by identifying genotype values of single nucleotide polymorphisms (SNPs) present within the DNA. The results in this example may include a sequence of genotypes corresponding to various SNP sites. In one embodiment, the genetic data extraction service server 125 may perform data pre-processing of the genetic data to convert raw sequences of base pairs to sequences of genotypes at target SNP sites. Since a typical human genome may differ from a reference human genome at only several million SNP sites (as opposed to billions of base pairs in the whole genome), the genetic data extraction service server 125 may extract only the genotypes at a set of target SNP sites and transmit the extracted data to the computing server 130 as the genetic dataset of an individual.

The computing server 130 performs various analysis of the genetic data, genealogical data, and users' survey responses to generate results regarding the phenotypes and genealogy of users of computing server 130. Depending on the embodiments, the computing server 130 may also be referring to as an online server, a personal genetic service server, a genealogy server, a family tree building server, and/or a social networking system. The computing server 130 receives genetic data from the genetic data extraction service server 125 and stores the genetic data in the data store of the computing server 130. The computing server 130 may analyze the data to generate results regarding the genetics or genealogy of users. The results regarding the genetics or genealogy of users may include the ethnic compositions of users, paternal and maternal genetic analysis, potential family relatives, ancestor information, analyses of DNA data, potential or identified phenotypes of users (e.g., diseases, traits, and other characteristics), etc. The computing server 130 may present or cause the user interface 115 to present the results to the users through a GUI displayed at the client device 110. The results may include graphical elements, textual information, data, charts, and other elements such as family trees.

In one embodiment, the computing server 130 also allows various users to create one or more genealogical profiles of the user. The genealogical profile may include a list of individuals (e.g., ancestors, relatives, friends, and other people of interest) who are added or selected by the user or suggested by the computing server 130 based on the genealogical records and/or genetic records. The user interface 115 controlled by or in communication with the computing server 130 may display the individuals in a list or as a family tree such as in the form of a pedigree chart. In one embodiment, subject to user's privacy setting and authorization, the computing server 130 may allow the user's genetic dataset to be linked to the user profile and to one or more of the family trees. The users may also authorize the computing server 130 to analyze their genetic dataset and allow their profiles to be discovered by other users.

Example Computing Server Architecture

Figure 2:
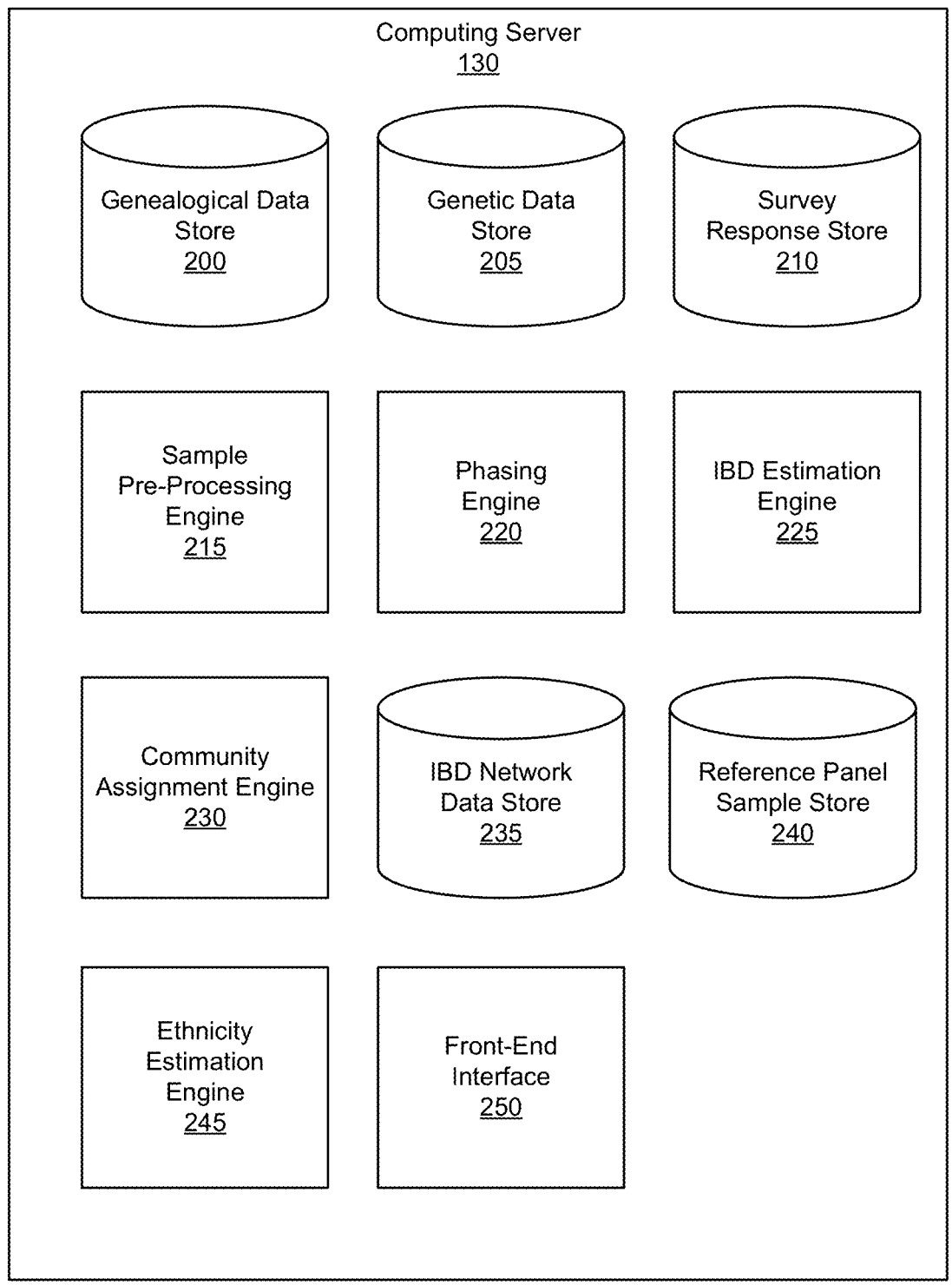
FIG. 2 is a block diagram of an architecture of an example computing system, in accordance with an embodiment.

FIG. 2 is a block diagram of an architecture of an example computing server 130, in accordance with an embodiment. In the embodiment shown in FIG. 2, the computing server 130 includes a genealogical data store 200, a genetic data store 205, a survey response store 210, a sample pre-processing engine 215, a phasing engine 220, an IBD estimation engine 225, a community assignment engine 230, an IBD network data store 235, a reference panel sample store 240, an ethnicity estimation engine 245, and a front-end interface 250. The functions of the computing server 130 may be distributed among the elements in a different manner than described. In various embodiments, the computing server 130 may include different components and fewer or additional components. Each of the various data stores may be a single storage device, a server controlling multiple storage devices, or a distributed network that is accessible through multiple nodes (e.g., a cloud storage system).

The computing server 130 stores various data of different individuals, including genetic data, genealogical data, and survey response data. The computing server 130 processes the genetic data of users to identify shared identity-by-descent (IBD) segments between individuals. The genealogical data and survey response data may be part of user profile data. The amount and type of user profile data stored for each user may vary based on the information of a user, which is provided by the user as she creates an account and profile at a system operated by the computing server 130 and continues to build her profile, family tree, and social network at the system and to link her profile with her genetic data. Users may provide data via the user interface 115 of a client device 110. Initially and as a user continues to build her genealogical profile, the user may be prompted to answer questions related to basic information of the user (e.g., name, date of birth, birthplace, etc.) and later on more advanced questions that may be useful for obtaining additional genealogical and survey data. The computing server 130 may also include survey questions regarding various traits, characteristics, preferences, habits, lifestyle, environment, etc. of the users.

Genealogical data may be stored in the genealogical data store 200 and may include various types of data that are related to tracing family relatives of users. Examples of genealogical data include names (first, last, middle, suffixes), gender, birth locations, date of birth, date of death, marriage information, spouse's information kinships, family history, dates and places for life events (e.g., birth and death), other vital data, and the like. In some instances, family history can take the form of a pedigree of that individual (e.g., the recorded relationships in the family). The family tree information associated with a user includes one or more specified nodes. Each node in the family tree represents the individual, an ancestor of the individual who might have passed down genetic material to the individual, and the individual's other relatives including siblings, cousins, offspring in some cases. Genealogical data may also include connections and relationships among users of the computing server 130. The information related to the connections among a user and her relatives that may be associated with a family tree may also be referred to as pedigree data or family tree data.

In addition to user-input data, genealogical data also may take other forms that are obtained from various sources such as public records and third-party data collectors. For example, genealogical records from public sources include birth records, marriage records, death records, census records, court records, probate records, adoption records, obituary records, etc. Likewise, genealogical data may include data from one or more of a pedigree of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, a motor vehicle database, and the like.

Furthermore, the genealogical data store 200 may also include relationship information inferred from the genetic samples stored in the genetic data store 205 and information received from the individuals. For example, the relationship information may include which individuals are genetically related, how they are related, how many generations back they share common ancestors, lengths and locations of IBD segments shared, which genetic communities an individual is a part of, variants carried by the individual, and the like.

The computing server 130 maintains genetic datasets of individuals in the genetic data store 205. A genetic dataset of an individual may be a digital dataset of nucleotide data and corresponding metadata. A genetic dataset may contain data of the whole or portions of an individual's genome. The genetic data store 205 may store a pointer to a location associated with the genealogical data store 200 associated with the individual. A genetic dataset may take different forms. In one embodiment, a genetic dataset may take the form of a base pair sequence of the sequencing result of an individual. A base pair sequence dataset may include the whole genome of the individual (e.g., obtained from a whole-genome sequencing) or some parts of the genome (e.g., genetic loci of interest).

In another embodiment, a genetic dataset may take the form of sequences of genetic markers. Examples of genetic markers may include target SNP sites (e.g., allele sites) filtered from the sequencing results. A SNP site may be associated with a unique identifier. The genetic dataset may be in a form of a diploid data that include a sequencing of genotypes, such as genotypes at the target SNP sites, or the whole base pair sequence that includes genotypes at known SNP sites that vary between individuals and other base pair sites that are not commonly associated with known SNP sites. The diploid dataset may be referred to as a genotype dataset or a genotype sequence. Genotype may have a different meaning in various context. In one context, an individual's genotype may refer to a collection of diploid alleles of an individual. In other contexts, a genotype may be a pair of alleles present on two chromosomes for an individual at a given genetic marker such as a SNP site.

A genotype at a SNP site may include a pair of alleles. The pair of alleles may be homozygous (e.g., A-A or G-G) or heterozygous (e.g., A-T, C-T). Instead of storing the actual nucleotides, the genetic data store 205 may store genetic data that are converted to bits. For a given SNP site, oftentimes only two nucleotide alleles (instead of all 4) are observed. As such, a 2-bit number may represent a SNP site. For example, 00 may represent homozygous first alleles, 11 may represent homozygous second alleles, and 01 or 10 may represent heterozygous alleles. A separate library may store what nucleotide corresponds to the first allele and what nucleotide corresponds to the second allele at a given SNP site.

A diploid dataset may also be phased into two sets of haploid data, one corresponding to a first parent side and another corresponding to a second parent side. The phased datasets may be referred to as haplotype datasets or haplotype sequence.

The computing server 130 may present various survey questions to its users from time to time. The responses to the survey questions may be stored at survey response store 210. The survey questions may be related to various aspects of the users and the users' family. Some survey questions may be related to users' phenotypes, while other may be related to environmental factors of the users.

For example, survey questions may concern health or disease-related phenotypes, such as questions related to the presence or absence of genetic diseases or disorders, inheritable diseases or disorders, or other common diseases or disorders that have family history as one of the risk factors, questions regarding any diagnosis of increased risk of any diseases or disorders, and questions concerning wellness-related issues such as family history of obesity, family history of causes of death, etc. The diseases identified by the survey questions may be related to single-gene diseases or disorders that are caused by a single-nucleotide variant, an insertion, or a deletion. The diseases identified by the survey questions may also be multifactorial inheritance disorders that may be caused by a combination of environmental factors and genes. Example of multifactorial inheritance disorders may include heart disease, Alzheimer's diseases, diabetes, cancer, and obesity. The computing server 130 may obtain data of a user's disease-related phenotypes from survey questions of health history of the user and her family and also from health records uploaded by the user.

Survey questions also may be related to other types of phenotypes such as traits and characteristics of the users. A survey regarding traits and characteristics may include questions related to eye color, iris pattern, freckles, chin types, finger length, dimple chin, earlobe types, hair color, hair curl, skin pigmentation, susceptibility to skin burn, bitter taste, male baldness, baldness pattern, presence of unibrow, presence of wisdom teeth, height, and weight. A survey regarding traits and characteristics also may include questions related to users' taste and smell such as the ability to taste bitterness, asparagus smell, cilantro aversion, etc. A survey regarding traits and characteristics may further include questions related to users' lactose tolerance, caffeine consumption, malaria resistance, norovirus resistance, muscle performance, alcohol flush, etc.

Computing server 130 also may present various survey questions related to environmental factors of users. In this context, an environmental factor may be a factor that is not directly connected to the genetics of the users. Environmental factors may include users' preferences, habits, and lifestyle. For example, a survey regarding users' preferences may include questions related to things and activities that user like or dislike, such as types of music a user enjoys, certain sports that a user plays, video games preferences, etc. Other questions may be related to the users' diet preference such as like or dislike a certain type of food. A survey related to habits and lifestyle may include questions regarding smoking habits, alcohol consumption and frequency, daily exercise duration, sleeping cycles and problems, hobbies, and travel preferences. Additional environmental factors may include diet amount (calories, macronutrients), physical fitness abilities (e.g. stretching, flexibility, heart rate recovery), family type (adopted family or not, has siblings or not, lived with extended family during childhood), property and item ownership (has home or rents, has smart phone or doesn't, has car or doesn't).

Surveys also may be related to other environmental factors such as geographical, social-economic, or cultural factors. Geographical questions may include questions related to the birth location, family migration history, town or city of users' current or past residence. Social-economic questions may be related to users' education level, income, occupations, self-identified demographic groups, etc. Questions related to culture may concern users' religions, native language, language spoken at home, customs, dietary practices, etc.

In addition to storing the survey data in the survey response store 210, the computing server 130 may store some responses that correspond to data related to genealogical and genetics respectively to genealogical data store 200 and genetic data store 205.

The survey response data, the genetic data, and the genealogical data may subject to the privacy and authorization setting from the users. For example, when presented with a survey question, a user may select to answer or skip the question. The computing server 130 may present users from time to time information regarding users' selection of the extent of information and data shared. The computing server 130 also may maintain and enforce one or more privacy settings for users in connection with the access of the user data. For example, the user may pre-authorize the access of the data and may change the setting as wish. The privacy settings also may allow a user to specify (e.g., by opting out, by not opting in) whether the computing server 130 may receive, collect, log, or store particular data associated with the user for any purpose. A user may restrict her data at various levels. For example, in one level, the data may not be accessed by the computing server 130 for purposes other than displaying the data in the user's own profile. In another level, the user may authorize anonymization of her data and participate in studies and researches conducted by the computing server 130 such as a large scale genetic study. In yet another level, the user may turn some portions of her genealogical data public to allow the user to be discovered by other users (e.g., potential relatives) and be connected in one or more family trees.

The sample pre-processing engine 215 receives and pre-processes data received from various sources to change the data into a format used by the computing server 130. For genealogical data, the sample pre-processing engine 215 may receive data from an individual via the user interface 115 of the client device 110. To collect the user data (e.g., genealogical and survey data), the computing server 130 may cause an interactive user interface on the client device 110 to display interface elements in which users can provide genealogical data and survey data. Additional data may be obtained from scans of public records. The data may be manually provided or automatically extracted via, for example, optical character recognition (OCR) performed on census records, town or government records, or any other item of printed or online material. Some records may be obtained by digitalizing written records such as older census records, birth certificates, death certificates, etc.

The sample pre-processing engine 215 may also receive raw data from genetic data extraction service server 125. The genetic data extraction service server 125 may perform laboratory analysis of biological samples of users and generate sequencing results in the form of digital data. The sample pre-processing engine 215 may receive the raw genetic datasets from the genetic data extraction service server 125. The human genome mutation rate is estimated to be $1.1*10^{-8}$ per site per generation. This leads to a variant approximately every 300 base pairs. Most of the mutations that are passed down to descendants are related to single-nucleotide polymorphism (SNP). SNP is a substitution of a single nucleotide that occurs at a specific position in the genome. The sample pre-processing engine 215 may convert the raw base pair sequence into a sequence of genotypes of target SNP sites. Alternatively, the pre-processing of this conversion may be performed by the genetic data extraction service server 125. The sample pre-processing engine 215 identifies autosomal SNPs in an individual's genetic dataset. For example, 700,000 autosomal SNPs may be identified in an individual's data and may be stored in genetic data store 205. Alternatively, in one embodiment, a genetic dataset may include at least 10,000 SNP sites. In another embodiment, a genetic dataset may include at least 100,000 SNP sites. In yet another embodiment, a genetic dataset may include at least 500,000 SNP sites. In yet another embodiment, a genetic dataset may include at least 1,000,000 SNP sites. The sample pre-processing engine 215 may also convert the nucleotides into bits. The identified SNPs, in bits or in other suitable formats, may be provided to the phasing engine 220 which phases the individual's diploid genotypes to generate a pair of haplotypes for each user.

The sample pre-processing engine 215 also may convert survey responses to standardized formats. For some responses, numerical representations may be used to present the phenotypes of the users obtained from surveys. For example, 1 may represent the presence of a phenotype while 0 may represent the absence of the phenotype. In another example, the computing server 130 may represent multiple phenotypes as 0, 1, 2, 3, etc. for each type of phenotype. For phenotypes that can be represented by a scale or a degree, the computing server 130 may also use numerical representations to record the phenotype.

The phasing engine 220 phases diploid genetic dataset into a pair of haploid genetic datasets. An individual's haplotype may refer to a collection of alleles (e.g., a sequence of alleles) that are inherited from a parent. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

Phasing may include a process of determining the assignment of alleles (particularly heterozygous alleles) to chromosomes. Owing to sequencing conditions and other constraints, a sequencing result often includes data regarding a pair of alleles at a given SNP site of a pair of chromosomes but may not be able to distinguish which allele belongs to which specific chromosome. The phasing engine 220 uses a genotype phasing algorithm to assign one allele to a first chromosome and another allele to another chromosome. The genotype phasing algorithm may be developed based on an assumption of linkage disequilibrium (LD), which states that haplotype in the form of a sequence of alleles tends to cluster together. The phasing engine 220 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as training sample because the correct phasing of the child is almost certain by comparing the child's genotypes to the parent's genetic datasets. The haplotype-cluster model may be generated iteratively along with the phasing process with a large number of unphased genotype datasets.

By way of example, the phasing engine 220 may use a directed acyclic graph model such as a hidden Markov model (HMM) to perform phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing engine 220 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. patent application Ser. No. 15/591,099, entitled "Haplotype Phasing Models," filed on Oct. 19, 2015, describes one possible embodiment of haplotype phasing.

The IBD estimation engine 225 estimates the amount of shared genetic segments between a pair of individuals based on phased genotype data (e.g., haplotype datasets) that are stored in the genetic data store 205. IBD segments may be segments identified in a pair of individuals that are putatively determined to be inherited from a common ancestor. The IBD estimation engine 225 retrieves a pair of haplotype datasets for each individual. The IBD estimation engine 225 may divide each haplotype dataset sequence into a plurality of windows. Each window may include a fixed number of SNP sites (e.g., about 100 SNP sites). The IBD estimation engine 225 identifies one or more seed windows in which the alleles at all SNP sites in at least one of the phased haplotypes between two individuals are identical. The IBD estimation engine 225 may expand the match from the seed windows to nearby windows until the matched windows reach the end of a chromosome or until a homozygous mismatch is found, which indicate the mismatch is not attributable to potential errors in phasing. The IBD estimation engine 225 determines the total length of matched segments, which may also be referred to as IBD segments. The length may be measured in the genetic distance in the unit of centimorgans (cM). The computing server 130 may save data regarding individual pairs who share a length of IBD segments exceeding a predetermined threshold (e.g., 6 cM), such as in the genealogical data store 200. U.S. patent application Ser. No. 14/029,765, entitled "Identifying Ancestral Relationships Using a Continuous stream of Input," filed on Sep. 17, 2013, and U.S. patent application Ser. No. 15/519,104, entitled "Reducing Error in Predicted Genetic Relationships," filed on Apr. 13, 2017, describe example embodiments of IBD estimation.

Typically, individuals who are closely related share a relatively large number of IBD segments, and the IBD segments tend to have greater lengths (individually or in aggregate across one or more chromosomes). In contrast, individuals who are more distantly related share relatively fewer IBD segments, and these segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity. For example, the IBD affinity may be measured in terms of the length of IBD segments between two individuals.

Community assignment engine 230 assigns individuals to one or more genetic communities. A genetic community may correspond to an ethnic origin or a group of people descended from a common ancestor. The granularity of genetic community classification may vary depending on embodiments and methods used in assigning communities. For example, in one embodiment, the communities may be African, Asian, European, etc. In another embodiment, the European community may be divided into Irish, German, Swedes, etc. In yet another embodiment, the Irish may be further divided into Irish in Ireland, Irish immigrated to America in 1800, Irish immigrated to America in 1900, etc. The community classification may also depend on whether a population is admixed or unadmixed. For an admixed population, the classification may further be divided based on different ethnic origins in a geographical region.

Community assignment engine 230 may assign individuals to one or more genetic communities based on their genetic datasets using machine learning models trained by unsupervised learning or supervised learning. In an unsupervised approach, the community assignment engine 230 may generate data representing a partially connected undirected graph. In this approach, the community assignment engine 230 represents individuals as nodes. Some nodes are connected by edges whose weights are based on IBD affinity between two individuals represented by the nodes. For example, if the total length of two individuals' shared IBD segments does not exceed a predetermined threshold, the nodes are not connected. The edges connecting two nodes are associated with weights that are measured based on the IBD affinities. The undirected graph may be referred to as an IBD network. The community assignment engine 230 uses clustering techniques such as modularity measurement (e.g., Louvain method) to classify nodes into different clusters in the IBD network. Each cluster may represent a community. The community assignment engine 230 may also determine sub-clusters, which represent sub-communities. The computing server 130 saves the data representing the IBD network and clusters in the IBD network data store 235. U.S. patent application Ser. No. 15/168,011, entitled "Discovering Population Structure from Patterns of Identity-By-Descent," filed on May 28, 2016, describes one possible embodiment of community detection and assignment.

The community assignment engine 230 may also assign communities using supervised techniques. For example, genetic datasets of known genetic communities (e.g., individuals with confirmed ethnic origins) may be used as training sets that have labeled of the genetic communities. Supervised machine learning classifiers, such as logistic regressions, support vector machines, random forest classifiers, and neural networks may be trained using the training set with labels. A trained classifier may distinguish binary or multiple classes. For example, a binary classifier may be trained for each community of interest to determine whether a target individual's genetic dataset belongs or does not belong to the community of interest. A multi-class classifier such as a neural network may also be trained to determine whether the target individual's genetic dataset most likely belongs to one of several possible genetic communities.

Reference panel sample store 240 stores reference panel samples for different genetic communities. Some individuals' genetic data may be the most representative of a genetic community. Their genetic datasets may serve as reference panel samples. For example, some alleles of genes may be over-represented (e.g., being highly common) in a genetic community. Some genetic datasets include alleles that are commonly present among members of the community. Reference panel samples may be used to train various machine learning models in classifying whether a target genetic dataset belongs to a community, in determining the ethnic composition of an individual, and in determining the accuracy in any genetic data analysis, such as by computing a posterior probability of a classification result from a classifier.

A reference panel sample may be identified in different ways. In one embodiment, an unsupervised approach in community detection may apply the clustering algorithm recursively for each identified cluster until the sub-clusters contain a number of nodes that is smaller than a threshold (e.g., contains fewer than 1000 nodes). For example, the community assignment engine 230 may construct a full IBD network that includes a set of individuals represented by nodes and generate communities using clustering techniques. The community assignment engine 230 may randomly sample a subset of nodes to generate a sampled IBD network. The community assignment engine 230 may recursively apply clustering techniques to generate communities in the sampled IBD network. The sampling and clustering may be repeated for different randomly generated sampled IBD networks for various runs. Nodes that are consistently assigned to the same genetic community when sampled in various runs may be classified as a reference panel sample. The community assignment engine 230 may measure the consistency in terms of a predetermined threshold. For example, if a node is classified to the same community 95% (or another suitable threshold) of times whenever the node is sampled, the genetic dataset corresponding to the individual represented by the node may be regarded as a reference panel sample. Additionally, or alternatively, the community assignment engine 230 may select N most consistently assigned nodes as a reference panel for the community.

Other ways to generate reference panel samples are also possible. For example, the computing server 130 may collect a set of samples and gradually filter and refine the samples until high-quality reference panel samples are selected.

The ethnicity estimation engine 245 estimates the ethnicity composition of a genetic dataset of a target individual. The genetic datasets used may be genotype datasets or haplotype datasets. For example, the ethnicity estimation engine 245 estimates the ancestral origins (e.g., ethnicity) based on the individual's genotypes or haplotypes at the SNP sites. To take a simple example of three ancestral populations corresponding to African, European and Native American, an admixed user may have nonzero estimated ethnicity proportions for all three ancestral populations, with an estimate such as [0.05, 0.65, 0.30], indicating that the user's genome is 5% attributable to African ancestry, 65% attributable to European ancestry and 30% attributable to Native American ancestry. The ethnicity estimation engine 245 generates the ethnic composition estimate and stores the estimated ethnicities in a data store of computing server 130 with a pointer in association with a particular user.

In one embodiment, the ethnicity estimation engine 245 divides a target genetic dataset into a plurality of windows (e.g., about 1000 windows). Each window includes a small number of SNP sites (e.g., 300 SNP sites). The ethnicity estimation engine 245 may use a directed acyclic graph model to determine the ethnic composition of the target genetic dataset. The directed acyclic graph may represent a trellis of an inter-window hidden Markov model (HMM). The graph includes a sequence of a plurality of levels. Each level, representing a window, include a plurality of nodes. The nodes representing different possibilities of labels of genetic communities (e.g., ethnicities) for the window. A node may be labeled with one or more ethnic labels. For example, a level includes a first node with a first label representing the likelihood that the window of SNP sites belongs to a first ethnicity and a second node with a second label representing the likelihood that the window of SNP sites belongs to a second ethnicity. Each level includes multiple nodes so that there are many possible paths to traverses the directed acyclic graph.

The nodes and edges in the directed acyclic graph may be associated with different emission probabilities and transition probabilities. An emission probability associated with a node represents the likelihood that the window belongs to the ethnicity labeling the node given the observation of SNP sites in the window. The ethnicity estimation engine 245 determines the emission probabilities by comparing SNP sites in the window corresponding to the target genetic dataset to corresponding SNP sites in the windows in various reference panel samples of different genetic communities stored in the reference panel sample store 240. The transition probability between two nodes represents the likelihood of transition from one node to another across two levels. The ethnicity estimation engine 245 determines a statistically likely path, such as the most probable path or a probable path that is at least more likely than 95% of other possible paths, based on the transition probabilities and the emission probabilities. A suitable dynamic programming algorithm such as the Viterbi algorithm or the forward-backward algorithm may be used to determine the path. After the path is determined, the ethnicity estimation engine 245 determines the ethnic composition of the target genetic dataset by determining the label compositions of the nodes that are included in the determined path. U.S. patent application Ser. No. 15/209,458, entitled "Local Genetic Ethnicity Determination System," filed on Jul. 13, 2016, describes an example embodiment of ethnicity estimation.

The front-end interface 250 may display various results determined by the computing server 130. The results and data may include the IBD affinity between a user and another individual, the community assignment of the user, the ethnicity estimation of the user, phenotype prediction and evaluation, genealogical data search, family tree and pedigree, relative profile and other information. The front-end interface 250 may also display results such as predictions of phenotypes and other characteristics of the users. The front-end interface 250 may be a graphical user interface (GUI) that displays various information and graphical elements. The front-end interface 250 may take different forms. In one case, the front-end interface 250 may be a software application that can be displayed at an electronic device such as a computer or a smartphone. The software application may be developed by the entity controlling the computing server 130 and be downloaded and installed at the client device 110. In another case, the front-end interface 250 may take the form of a webpage interface of the computing server 130 that allows users to access their family tree and genetic analysis results through web browsers. In yet another case, the front-end interface 250 may provide an application program interface (API).

Example Recommender System

Figure 3:
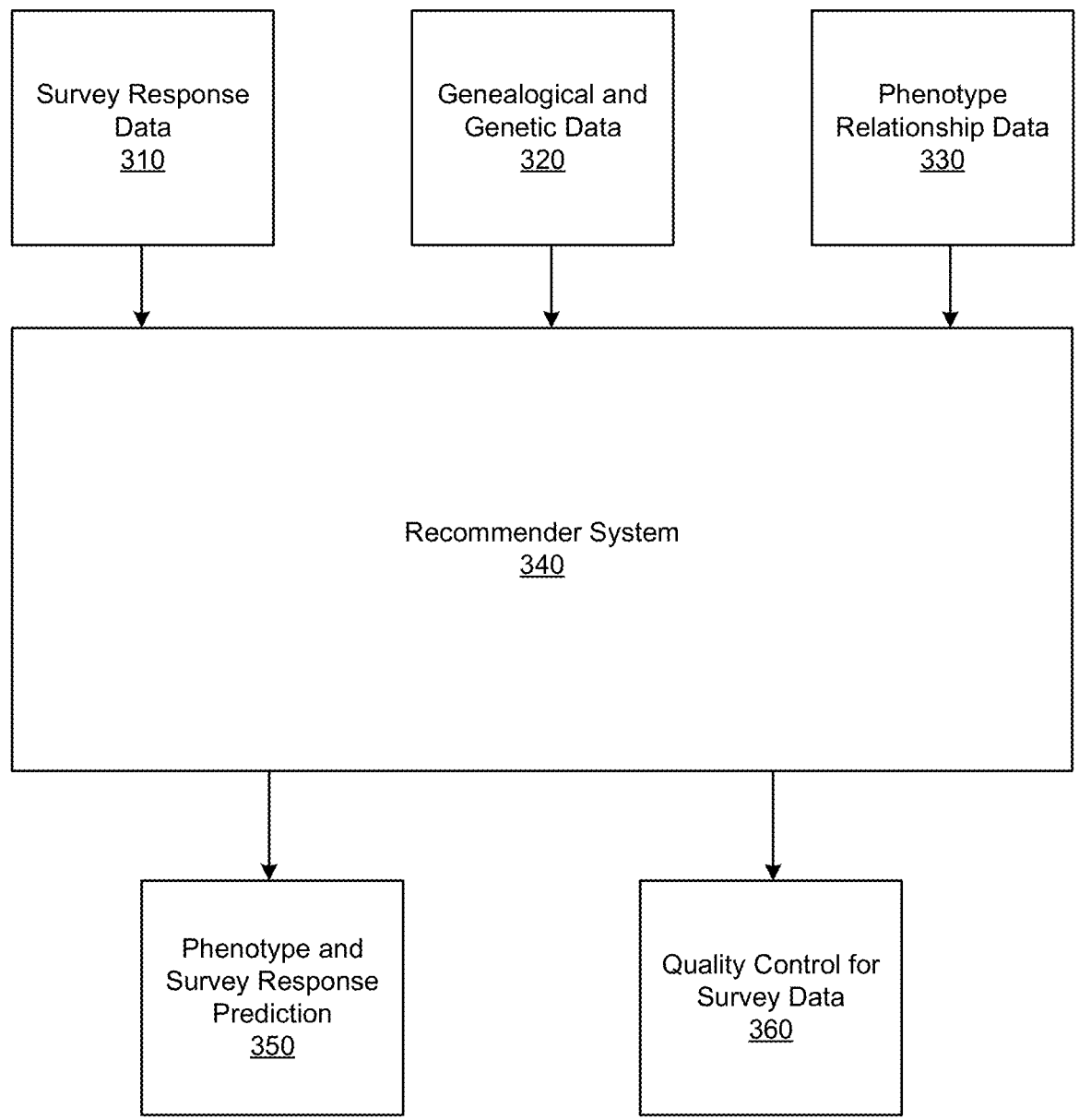
FIG. 3 is a block diagram illustrating an example recommender system, in accordance with an embodiment.

FIG. 3 is a block diagram illustrating an example recommender system that may be used to predict phenotypes and/or survey responses of users and/or to perform quality control for the survey data, in accordance with an embodiment. A computing system 130 may retrieve, from a storage medium such as a memory, various types of data, including survey response data 310, genealogical and genetic data 320, and phenotype inter-relationship data 330. Based on the data, the computing system 130 may use a recommender system 340 to generate predictions 350 of one or more individuals' phenotypes and/or survey responses of the individuals (whether to verify the responses or to predict unanswered responses). The computing system 130 also may use the recommender system 340 to perform quality control 360 of survey data received by the computing system 130. The recommender system 340 may be outside of the computing server 130 or be a component of the computing server 130. The recommender system 340 may be one or more software algorithms or may additionally include hardware described in FIG. 10 to implement the software. In various embodiments, different types of a recommender system 340 may be used. Depending on the type, the recommender system 340 may rely on one or more types of data 310, 320 and 330. For example, in one embodiment, the recommender system 340 may rely on only survey response data 310. In another embodiment, the recommender system 340 may rely on all three types of data 310, 320 and 330. Also, some of the data may be pre-processed before the data is provided to the recommender system 340.

Survey response data 310 may correspond to the data stored in survey response store 210. Survey responses may include data regarding survey questions related to individuals' phenotypes and environmental factors. The computing server 130 may convert text and other data formats of the survey responses and phenotypes indicated in the responses to a standardized format such as numerical representations. By way of example, the computing server 130 may present survey questions in different forms and receive responses in various formats. A response may be in a binary value. For instance, a user may select whether she has or does not have lactose intolerance. A response also may be selected from one of several predetermined answers. For instance, the computing server 130 may provide a limited choice of eye color for users to select. A response further may take the form of a scale such as the response for the height of a user. A response further may be an open-ended response. For example, a user may respond to a lifestyle question related to activities she enjoys with a paragraph describing her lifestyle and preferences. The computing server 130 may store the responses in text in the survey response store 210, but may also convert the responses in numerical representations. For instance, the computing server 130 may store the actual eye color or store the numerical representation of the color. In some embodiments, the numerical representations of the phenotypes of users as indicated by the survey responses may be used in a recommender system 340 such as a collaborative filtering system that will be discussed in further details below.

Genealogical and genetic data 320 may correspond to data stored in genealogical data store 200 and genetic data store 205. The genealogical and genetic data 320 may define or estimate relationships among different individuals. The computing server 130 may use a recommender system 340 to predict a phenotype of a target individual based on individuals who are similar to the target individual. The computing server 130 may define the similarity among individuals based on the relationships as indicated by the genealogical and genetic data 320.

The computing server 130 may analyze the relationships among different phenotypes of interest to generate phenotype relationship data 330. The presence or absence of certain phenotypes may be correlated. The computing server 130 may determine the correlations and other relationships of various phenotypes, genes, and other environmental factors based on studies in scientific literature such as genome-wide association studies (GWAS) and also based on the survey response data 310. For example, scientific literature may provide the correlation between an expression of a phenotype and a certain gene or the correlation between the expression of two phenotypes together. The computing server 130 may also correlate genetic data with other genetic data, e.g., the GWAS for hair color and GWAS for eye color may be correlated. In another example, the computing server 130 may study the survey responses of individuals to determine the correlation between the expression of two phenotypes (e.g., hair color and eye color may be correlated). The computing server 130 may represent those correlations or relationships in an n-dimensional vector space. For example, each phenotype of interest may be represented by embedding vectors with multiple features. An example feature of the vector, which may correspond to a dimension of the vector, may represent the degree of correlation or relationship between the phenotype of interest and another thing, such as another phenotype, gene, environment factor. The numerical representation of the degree of correlation or relationship may be converted from results discussed in the literature or from the study of survey responses. The relationships among those phenotypes of interests may be further studied using the vector space and be input into the recommender system.

The recommender system 340 may be of a different type. For example, the recommender system 340 may be matrix-based, cluster-based, or hybrid based that combines the matrix-based approach and the cluster-based approach. In general, in a matrix-based approach, the recommender system 340 may construct a matrix that arranges a set of individuals in the first dimension of the matrix (e.g., rows) and a set of phenotypes in the second dimension of the matrix (e.g., columns). The elements in the matrix may be numerical representations of the individuals' phenotypes, which may be obtained from survey responses or other suitable sources. Some elements may be missing in the matrix. The missing elements may represent certain undetermined phenotypes of individuals in which the recommender system 340 does not have information. The recommender system 340 may determine a prediction of an undermined phenotype based on other phenotypes of the target individual and also based on one or more other individuals' phenotypes. For example, techniques such as matrix factorization may be used to impute missing elements by assuming that the phenotypes can be embedded using a number of latent factors. A matrix-based approach may be an example of collaborative filtering. Generally, collaborative filtering may predict a target phenotype and/or survey response based on other phenotypes of the target individual and based on at least another individual's phenotypes as represented in numerical representations in a matrix. However, not every collaborative filtering approach in this disclosure may use matrix factorization in predicting the value of the target phenotype.

In general, a cluster-based approach may predict the expression of a phenotype of a target individual based on similarity. A cluster-based approach may rely on the expression of same phenotype of similar individuals whose similarity is defined in terms of genealogy and/or genetics. Alternatively, or additionally, a cluster-based approach may also rely on the target individual's expression of other phenotypes and the relationships among the phenotypes as indicated in the phenotype relationship data 330 to predict the expression of a target phenotype. A recommender system 340 that uses a cluster-based approach may use a feature vector to represent an individual or a phenotype. The recommender system 340 may preform clustering to identify individuals that are similar and/or phenotypes that are similar.

The cluster-based approach may also be referred to as a similarity approach. In various cases, how similarity is defined may vary based on different genealogy or genetic data. For example, in one case, the computing server 130 may use family tree data of the target individual to identify close relatives, such as cousins within a certain degree, as the similar individuals of the target individual. In another case, the computing server 130 may use the ethnicity estimation engine 245 to determine ethnicity compositions of various individuals and define similarity based on the ethnicity compositions. In yet another case, the computing server 130 may use IBD estimation engine 225 to determine the length of IBD segments shared between the target individual and another candidate similar individual. If the length of IBD segments shared between the target individual and the candidate exceeds a threshold, the computing server 130 may identify the candidate as a similar individual. In yet another case, the computing server 130 may use community assignment engine 230 to identify a community or a sub-community to which the target individual belongs. Other individuals who belong to the same community or the same sub-community may be identified as the individuals who are similar to the individual. In yet another case, the computing server 130 may use genealogical data such as the place of birth, the year of birth, etc. to define similarity. In an embodiment, the computing server 130 in a hybrid approach may combine two or more of the above data and approaches to define similarity. Other suitable ways to define similarity based on various types of genealogical and genetic data 320 are also possible. Survey responses and environmental factors may also be used to determine similarity. For example, one or more factors regarding smoking habits, alcohol consumption and frequency, daily exercise duration, sleeping cycles and problems, hobbies, and/or travel preferences might also be used as features in feature vectors to define similarity among individuals.

In a hybrid approach, the recommender system 340 may combine a cluster-based approach with a matrix-based approach. For example, the cluster-based approach may be used to reduce the sparsity (e.g., the number of missing elements) in the matrix and other types of collaborative filtering, e.g., matrix factorization, may subsequently be applied. Each of the different types of recommender system 340 will be discussed in further details below.

While various types of the recommender system 340 may be classified as cluster-based approaches, matrix-based approaches, and hybrid approaches, a recommender system 340 may also be classified based on the source of information it uses. For example, for cluster-based approaches that rely on information outside of the values used in a collaborative filtering matrix, such as matrix 510 shown later in FIG. 5, those recommender systems may be referred to as content-based approaches.

The recommender system 340 may be used to generate predictions 350 of phenotypes and/or survey responses. Given the genetic information of a set of individuals, their answers to survey questions, and other data such as sex, age, birth locations (e.g., data from 310, 320, and 330), the computing server 130 may use the recommender system 340 to predict phenotypes of individuals. For example, a set of individuals have answered questions on skin pigmentation, freckles, hair colors, and the likelihood of getting a sunburn. However, not all individuals in the set answer all of the questions. The set of individuals may be related or be similar to each other on different levels (e.g., being close relatives, being distant relatives, belong to the same genetic community, etc.). Using the recommender system 340, the computing server 130 predicts a phenotype such as likelihood to get sunburn from a target individual's answer to other survey questions and based on other similar individuals' answers to different survey questions. In another example, hypertension is a health phenotype of interest and is known to be correlated with certain lifestyle behaviors such as smoking and be correlated with other health metrics such as body mass index (BMI). Hypertension may also be heritable at some levels. Using a recommender system 340, the computing server 130 may predict whether a target individual has hypertension or not based on various genetic data and environmental data.

The recommender system 340 also may enable quality control 360 of survey data by detecting abnormality pattern in survey responses and may determine the noise levels in survey data. For example, a set of individuals have answered questions on skin pigmentation, freckles, hair colors, and the likelihood of getting a sunburn. From the phenotype relationship data 330, the computing server 130 may expect that a person's skin pigmentation, freckles, and hair color can influence their likelihood of getting a sunburn. A recommender system 340 may be used to predict the last trait from the first three traits combined with the genetic information of survey takers and prior knowledge of different traits. If the prediction is accurate, then the survey behaves as expected. This process may be used as a quality check for the survey data that the computing server 130 collects. In another example, a set of individuals have answered questions on skin pigmentation, freckles, hair colors, and whether the individuals taste cilantro as soapy. From the phenotype relationship data 330, the computing server 130 may expect that a person's skin pigmentation, freckles, and hair color should have no correlation with the taste of cilantro. However, if a recommender system 340 may still be used to predict the last trait from the first three traits with accuracy, then the survey may not behave as expected. This process may be used to identify potential sources of errors in the survey process, such as how the question is asked, how the survey takers understand the choices. Survey questions may be adjusted or removed based on the quality control study.

Example Matrix Based Collaborative Filtering Recommender System

Figure 4:
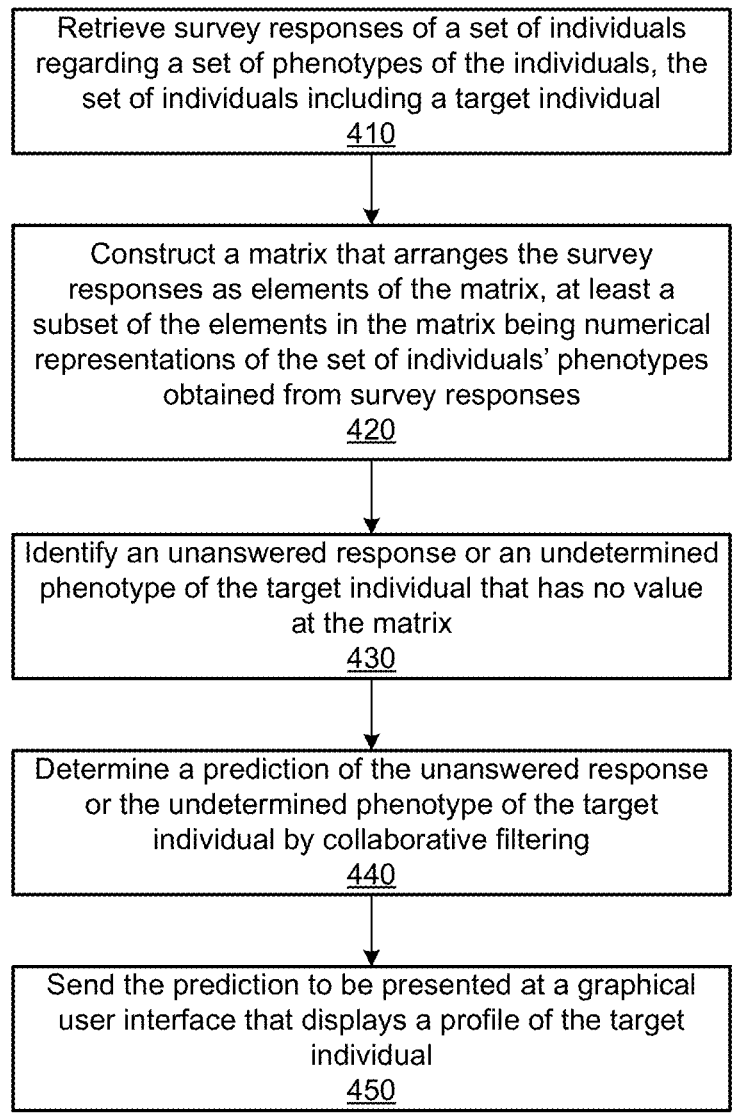
FIG. 4 is a flowchart depicting an example process of using matrix-based collaborative filtering to predict an undetermined phenotype, in accordance with an embodiment.
Figure 5:
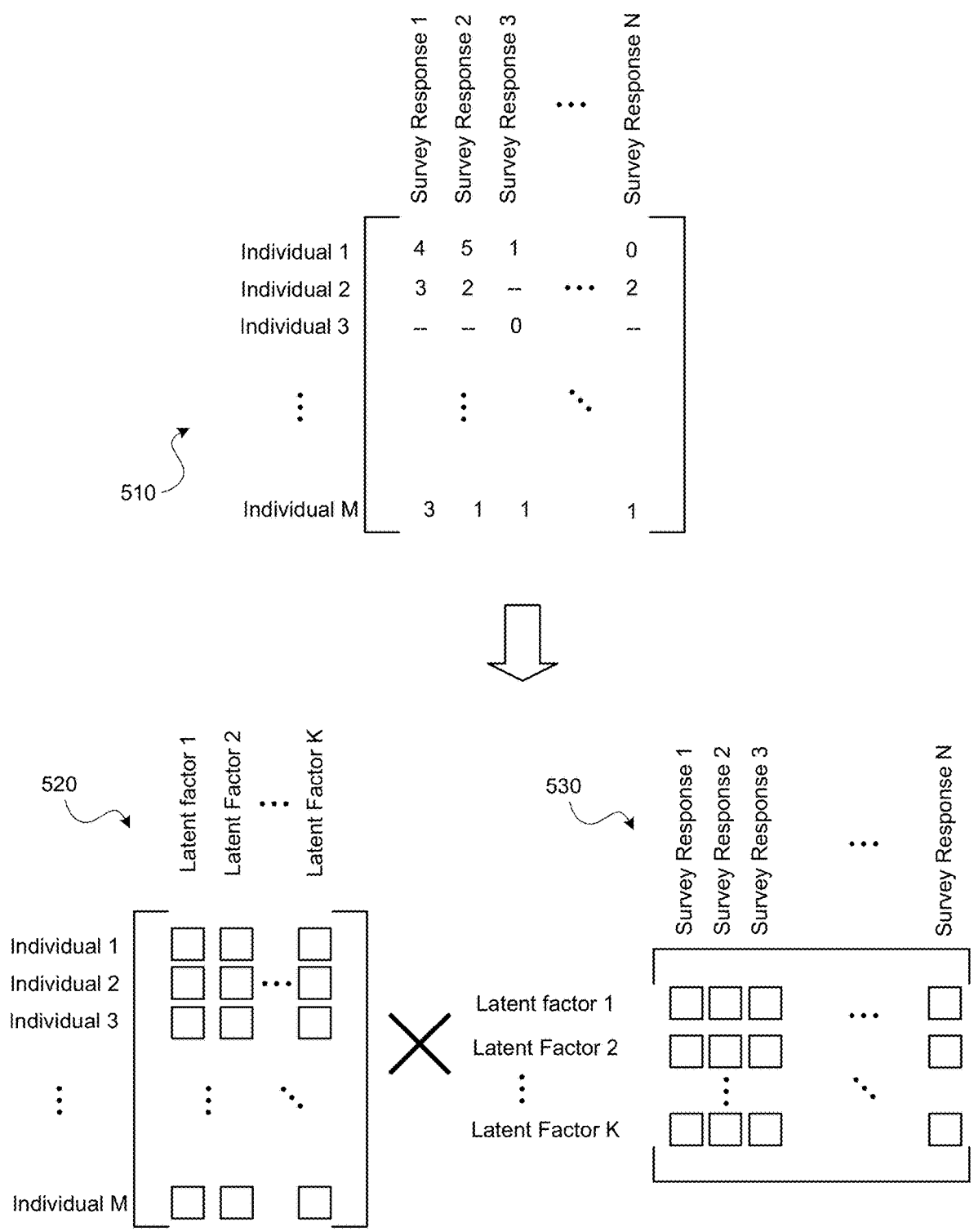
FIG. 5 is a diagram illustrating matrices used in collaborative filtering, in accordance with an embodiment.

FIG. 4 is a flowchart depicting an example process of using matrix based collaborative filtering to predict an undetermined phenotype of a target individual, in accordance with an embodiment. FIG. 5 is a diagram illustrating matrices used in collaborative filtering, in accordance with an embodiment.

A recommender system 340 may use a matrix based approach to predict undetermined phenotypes of a target individual as well as survey responses of the target individual. In one embodiment, the recommender system 340 may retrieve 410 survey responses a set of individuals from a storage medium, such as a memory, of the computing server 130. The set of individuals includes the target individual. The survey responses may include responses to different types of questions. At least some of the survey responses are related to a set of phenotypes of the individuals. Some other questions may be related to environmental factors of the individuals. For example, one or more of the survey responses may be related to one of the following: an appearance trait question, a social-economical question, a cultural question, a preference question, a geographical question, a health-related question, or a family health history question. The retrieved data may take the form of numerical representations of the survey responses. Alternatively, or additionally, the recommender system 340 may convert the survey responses to standardized numerical representations. In addition to the survey responses, the recommender system 340 may retrieve other data that include genetics, phenotypes and/or environmental factors from other sources, such as the genealogical data store 200 and the genetic data store 205.

The recommender system 340 may construct 420 a matrix that arranges the survey responses as elements of the matrix. Various techniques and data structure, such as tables, linked lists, tensors, or other similar data structures may also be used to construct a matrix. At least a subset of the elements in the matrix may be numerical representations of the set of individuals' phenotypes obtained from survey responses. In one embodiment, the matrix may include additional elements that represent other data, such as environmental factors, included in other survey responses and other data that include the genetics, phenotypes and/or environmental factors of the set of individuals retrieved from other sources.

FIG. 5 shows an example matrix 510 that arranges the survey responses as elements of the matrix, in accordance with an embodiment. The matrix 510 may be a rectangular matrix that includes M by N elements. The matrix 510 arranges the set of individuals (individual 1, individual 2, . . . , individual M) in the first dimension of the matrix. In some cases, M and N can both be larger than 1000. In some cases, M and N can be larger than 10,000. The first dimension as shown in FIG. 5 may be the rows of the matrix but, in other embodiments, the first dimension may also be the columns. The matrix 510 arranges the survey responses (survey response 1, survey response 2, . . . , survey response N) in the second dimension of the matrix, which may be the columns in FIG. 5 but may also be the rows in other embodiments. While matrix 510 shows "Survey Responses" as an example of things that are arranged in the second dimension, the values could also be phenotypes of the individuals or values of environmental factors of the individuals. In other words, the elements of the matrix 510 may be numerical representations of the phenotype expressions, survey responses, or other traits and characteristics of the individuals. For example, the element at coordinate (2, 1) has a value "3," which may be the numerical representation of one of the possible choices in the survey response 1 that was answered by the individual 2. Some of the elements are undetermined, which do not have a value in the matrix and are represented by "--" in FIG. 5. Those are values that are associated with an unanswered survey response, an unknown phenotype of an individual, etc. In some embodiments, the recommender system 340 may also use other values, such as 0, to represent the unanswered survey response. Unanswered survey responses may correspond to survey questions that were presented to an individual but not answered by the individual and survey questions that correspond to survey questions that are never presented to the individual. The number of undetermined elements in a matrix may correspond to the sparsity of the matrix.

The recommender system 340 may identify 430 an unanswered response or an undetermined phenotype of a target individual. The matrix has no value at the particular element that corresponds to the unanswered response or the undetermined phenotype of the target individual. For example, the survey response 2 of the individual 3 in matrix 510 may be an undetermined phenotype.

The recommender system 340 may determine 440 a prediction of the unanswered response or the undetermined phenotype of the target individual by collaborative filtering. Collaborative filtering uses values of other phenotypes or other survey responses of the target individual and phenotypes or survey responses of other individuals represented in the matrix to predict the value of the unanswered response or the undetermined phenotype. In one case, the collaborative filtering is based on other phenotypes of the target individual and based on at least another individual's phenotypes as represented in numerical representations in the matrix. In other cases, two or more other individuals' phenotypes are used in collaborative filtering. After the prediction is generated, the recommender system 340 may store the prediction and associate the prediction with the user profile of the target individual. When the target individual logs on to a genealogical and/or personal genetic system provided by the computing server 130, the recommender system 340 may send 450 the prediction of the undetermined phenotype or the unanswered response to the user interface 115, such as a GUI, that displays a profile of the target individual. For example, the recommender system 340 may cause the user interface 115 to display a result that the target individual may have a higher chance of having a certain disease. The recommender system 340 may also compare the prediction to the analysis of the genetic data of the target individual to verify or assess the prediction.

FIG. 5 illustrates an example matrix based approach that makes a prediction of one or more undetermined values in the matrix 510 based on other values using matrix factorization, in accordance with an embodiment. The matrix factorization approach may also be referred to as a latent-factor-based approach. The recommender system 340 may factorize the matrix into two or more lower dimensionality matrices that include values related to a set of latent factors. In the particular example shown in FIG. 5, the matrix 510 may be factorized into two lower dimensionality matrices 520 and 530. The matrix 520 has M by K elements and the matrix 530 has K by N elements. In one embodiment, K is smaller than both M and N so that matrices 520 and 530 both have a lower dimension than the matrix 510. The multiplication product of the matrices 520 and 530 is the matrix 510 or approximates to the values in the matrix 510. The matrices 520 and 530 are related by a set of latent factors. For example, the first lower dimensionality matrix 520 arranges the set of individuals in the first dimension (e.g., rows) of the matrix 520 and arranges the set of latent factors in the second dimension (e.g. columns) of the matrix 520. The second lower dimensionality matrix 530 arranges the set of latent factors in the first dimension (e.g., rows) of the matrix 530 and arranges the set of survey responses (e.g., including phenotypes and/or environmental factors) in the second dimension (e.g., columns) of the matrix 530.

After the factorization, the recommender system 340 may determine one or more predictions based on a set of values of the latent factors corresponding to the target individual. By way of example, if the survey response 2 of individual 3 in matrix 510 is the undetermined value that the recommender system 340 attempts to predict using collaborative filtering, the recommender system 340 may use the set of latent factors associated with individual 3 to determine the value of the prediction. The set of latent factors associated with individual 3 may be represented in matrix 520 as the third row of values associated with individual 3. To determine the value of the prediction for the survey response 2, the recommender system 340 may multiply the third row of values associated with individual 3 in matrix 520 with the second column of values, which represents the relationship between the set of latent factors and the survey response 2, in the matrix 530. The product of the multiplication may be the value of the prediction. The recommender system 340 can map the numerical value to the survey responses or phenotypes to determine the prediction of the survey response or the phenotype associated with the target individual.

The recommender system 340 may use various suitable factorization techniques to perform the factorization. Techniques such as single value decomposition, non-negative factorization, probabilistic factorization, deep learning may be used to perform the factorization. The number of latent factors used may depend on the matrix. Increasing the number of latent factors may reduce the training error in machine learning but may overfit the data. One or more processors of the recommender system 340 may use a machine learning technique to perform the factorization. The product of two lower dimensionality matrices (e.g., 520 and 530) may produce an approximation matrix of the original matrix. A cost function may be defined as the total differences between the elements in the original matrix and the corresponding elements in the approximation matrix. The difference between an element in the original matrix and the corresponding element in the approximation matrix may be defined as the absolute value of the difference or the square difference. The recommender system 340 may divide the known values in the original matrix into a training set and a testing set. In the training, the cost function may compute the total differences for the elements in the training set by comparing the approximation values and the actual values that are known in the training set. A processor may use coordinate descent to iteratively adjust the values in the elements of the lower dimensionality matrices to reduce the value of the cost function by adjusting the elements in the matrices 520 and 530. Training may be completed if the value of the cost function no longer improves (e.g., convergence has been reached) or after a predetermined number of iterations. The recommender system 340 may use the trained model that include the two lower dimensionality matrices to predict values in the testing set to determine the performance of the training. If the training has a low error while the testing has a high error, the recommender system 340 may reduce the number of latent factors and re-perform the training.

Besides using collaborative filtering to predict a phenotype, the recommender system 340 may also use collaborative filtering to perform quality control of survey responses. Using the matrix-based approach, the recommender system 340 may treat some of the survey responses of one or more individuals in addition to the target individual as undetermined and predict those survey responses using collaborative filtering, even though those survey questions may have been answered by the individuals. The recommender system 340 may compare the predicted survey responses to the actual survey responses of the individuals to determine the reliability of the actual survey responses. The reliability may be represented by a metric that compares the expected accuracy of the prediction and the actual accuracy of the prediction. For example, if the survey response is related to a phenotype that is highly correlated to a set of other phenotypes, the expected accuracy of the prediction should be high. In another example, if the survey response is related to a phenotype that is not correlated to a set of other phenotypes, the expected accuracy of the prediction should be low. Hence, if the actual accuracy of the prediction is high while the expectation is low, the reliability metric may reflect a low value because the prediction results are inconsistent with the expectation. Based on the determined reliability, the recommender system 340 may identify a survey question whose responses have a reliability that is lower than a threshold. In turn, the recommender system 340 may adjust or remove the survey question from the system.

Example Cluster-Based Recommender System

Figure 6A:
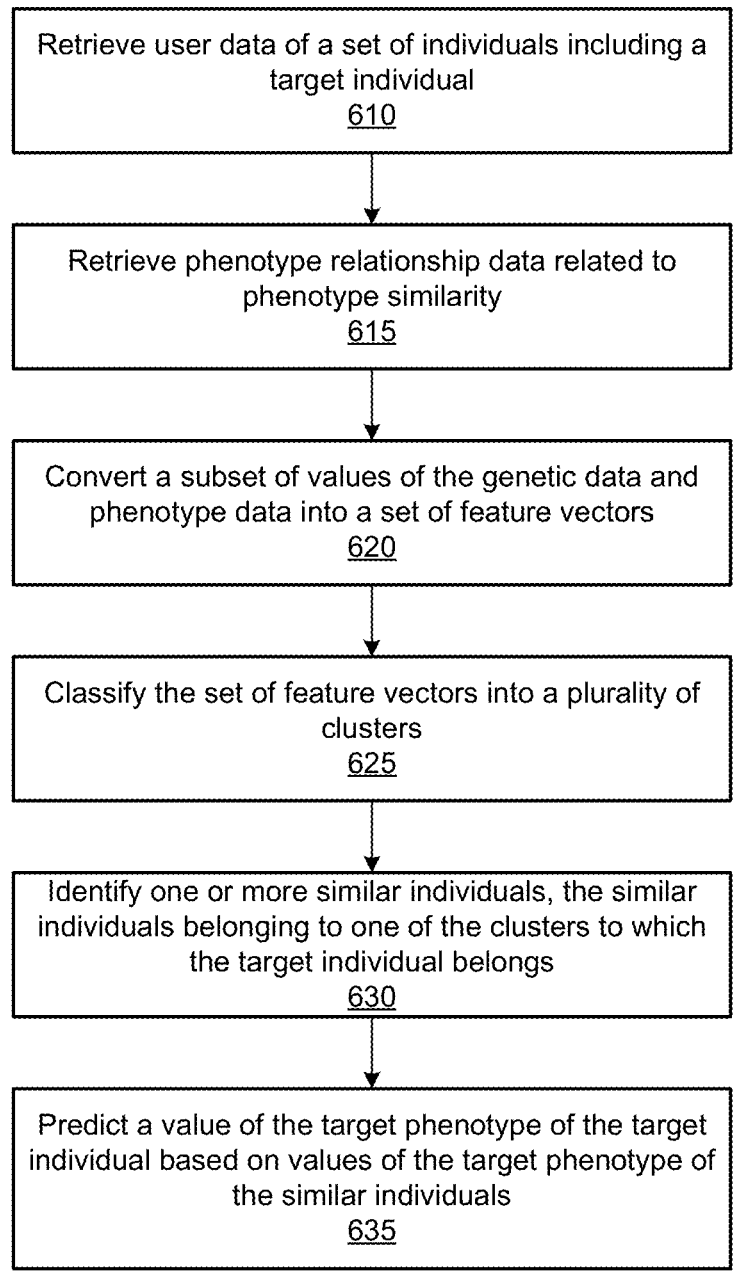
FIG. 6A is a flowchart depicting an example process of using a cluster-based recommender system, in accordance with an embodiment.

FIG. 6A is a flowchart depicting an example process of using a cluster-based recommender system to predict an undetermined phenotype (or an unanswered survey response) of a target individual, in accordance with an embodiment. In a cluster-based recommender system, the prediction of an undetermined phenotype may be based on the same phenotype of similar individuals. Alternatively, or additionally, a cluster-based approach may be based on the target individual's expressions of other phenotypes and the relationships between the target phenotype to be predicted and other phenotypes.

A recommender system 340, which may be part of the computing server 130 or outside of the computing server 130, may retrieve 610 user data of a set of individuals, which includes one or more target individuals. The user data may include genetic data, phenotype data, and/or survey response data. The data retrieved may also include genealogical data that describes relationships among the set of individuals.

Different sources of user data may be retrieved. For example, in a content-based approach of a cluster-based recommender system, information outside of a collaborative filtering matrix, such as matrix 510, may be used. In a collaborative filtering recommender system that relies on the cluster-based approach, information of a collaborative filtering matrix, such as a column or a row in matrix 510, may be used. In other cluster-based recommender systems, information from both inside and outside a collaborative filtering matrix may be used.

Figure 7:
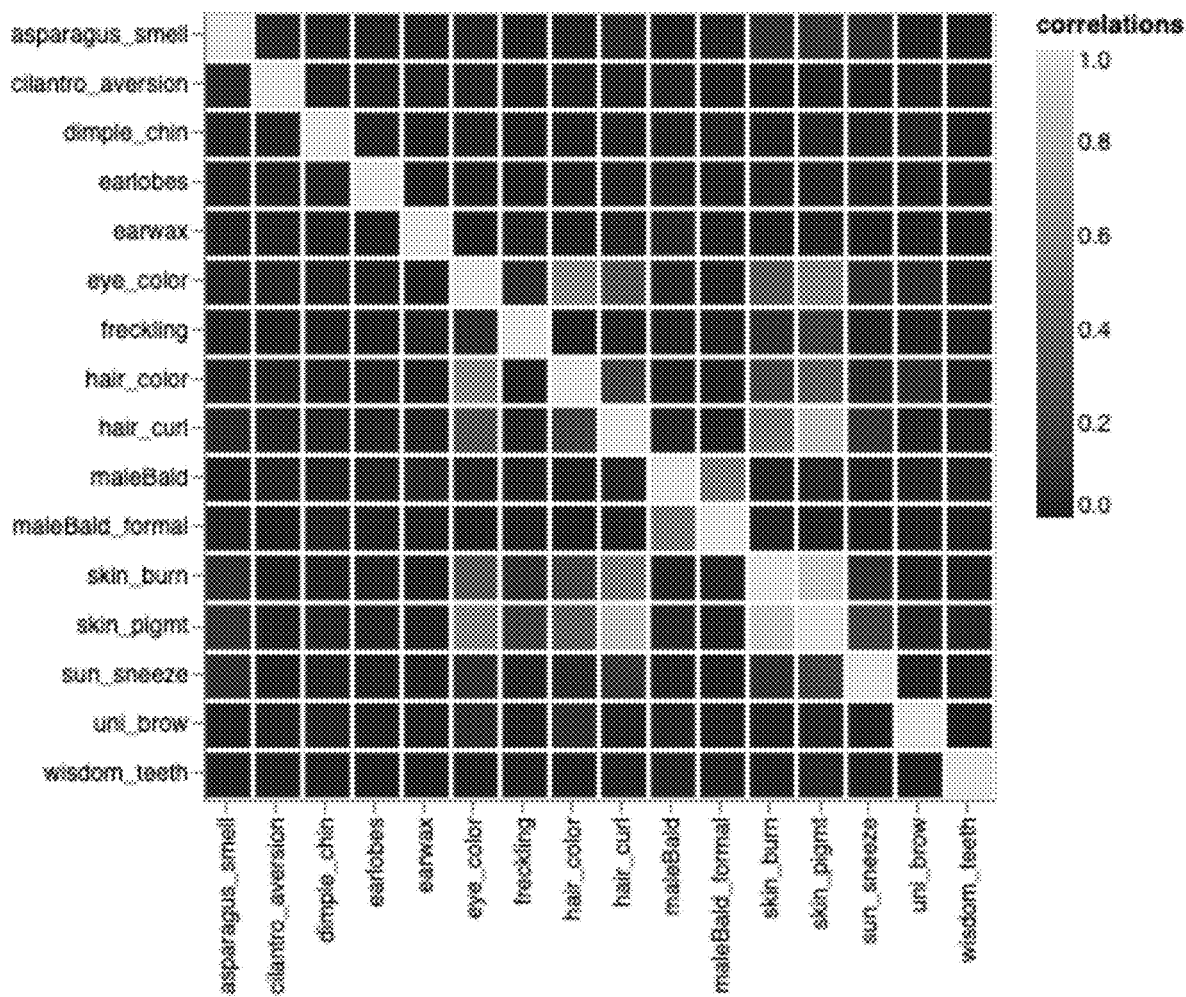
FIG. 7 is a chart showing an example study of correlations among different phenotypes, in accordance with an embodiment.

In some cases, the recommender system 340 may additionally retrieve 615 phenotype relationship data such as literature data that describe relationships among phenotypes as studied in scientific literature. For example, the correlation between target phenotype and other phenotypes may be determined from relationships between genotype data or genetic data in the literature, such as gene regulatory similarity, pathway similarity, or GWAS similarity. The recommender system 340 may also generate the relationships based on its own data, such as conducting a correlation study as shown in FIG. 7 based on data obtained from survey responses. Those correlation as studied may be converted to numerical values or formulas.

The recommender system 340 may convert 620 a subset of values of the data retrieved in step 610 and/or step 615 into a set of feature vectors. Each feature vector may correspond to an individual. A set of feature vectors may be used to represent the set of individuals. Each feature vector may include a plurality of features (e.g., different dimensions of the vectors). A feature may be a numerical representation of the genetic data of the individual or a numerical representation of the phenotype data of the individual. As such, a feature vector may include one or more numerical representations of the genetic data of the individual and one or more numerical representations of the phenotype data of the individual. A feature vector may also include numerical representations of other types of data.

Various features may be included in the feature vector. One or more of genetic data, phenotype data, survey response data, and/or literature data may be used as or be converted to feature values. In one embodiment, all of those types of data are included in generating various features. In another embodiment, some specific type of data is used. For example, in another case, a feature in the set of feature vectors is determined based on a length of identity-by-descent (IBD) segments shared between two individuals. In yet another case, a feature in the set of feature vectors is determined based on an ethnicity composition of a particular individual. The ethnicity composition may be determined by the ethnicity estimation engine 245. In yet another case, a feature in the set of feature vectors is determined based on a relationship between the genetic data of a particular individual and a phenotype as indicated in science literature. Other suitable features may also be used in the set of feature vectors, such as those in relationship with defining similarity as discussed above in association with FIG. 3.

In various sub-types of cluster-based approaches, a recommender system 340 may use different types of data in constructing the feature vectors. For example, values of features may be generated from information outside of the values in a collaborative filtering matrix, such as one shown in FIG. 5. In such case, the sub-type may be referred to as a content-based approach. In a content-based approach, the recommender system 340 may convert data from genetic data and phenotype data of a set of individuals to features. In another content-based approach, the recommender system 340 may additionally include literature data and other phenotype relationship data as features of the feature vectors. In another embodiment, a sub-type of cluster-based approach may be classified as collaborative filtering, which may predict a phenotype expression of a target individual by examining the phenotypes of similar individuals in terms of the set of phenotypes expressed as represented in a collaborative filtering matrix. This approach may also be referred to individual-based collaborative filtering. In yet another embodiment, the collaborative filtering process may take with a phenotype, find individuals who have information on that phenotype, examine the individuals' other phenotypes, and make predictions of the phenotype of the target individual. This approach may be referred to as phenotype based collaborative filtering.

The recommender system 340 may represent the feature vectors in an n-dimensional space. The recommender system 340 may classify 625 the set of feature vectors into a plurality of clusters. Each cluster may include one or more feature vectors representing one or more individuals. As such, the individuals in the set are classified into different clusters. Any suitable clustering techniques, such as K-Means clustering, mean-shift clustering, hierarchical clustering, community detection algorithms (e.g. Louvain method), may be used. The recommender system 340 may also define the differences or similarity among feature vectors based on different measurements, such as Euclidean distance, cosine similarity, etc.

The recommender system 340 may identify 630 one or more individuals who are similar to the target individual. Similar individuals may be defined differently. In one embodiment, the recommender system 340 may identify individuals who belong to one of the clusters to which the target individual belongs as the similar individuals. For example, the features in generating the feature vectors may be related to the shared IBD segments among the individuals. The identified similar individuals may belong to an IBD genetic community to which the target individual belongs. In another example, the features in generating the feature vectors may be related to pedigree data between different individuals. As such, the identified similar individuals may be relatives as indicated by the pedigree data. Other suitable ways to define similarity is also possible, such as using survey responses and/or environmental factors as discussed above. The cluster-based recommender system that relies on similar individuals may also be referred to as a neighborhood-based approach.

The recommender system 340 may predict 635 the value of the target phenotype of the target individual based on values of the target phenotype of the similar individuals. The predicted value may be an average of the values of the target phenotype of the similar individuals. In one case, the average may be weighted average with individuals that are evaluated as more similar to the target individual being weighted more heavily. For example, the similarity may be defined based on lengths of shared IBD segments and individuals with longer shared IBD segments may be weighted more heavily.

In some embodiments, the determination of the predicted value may also be based on other phenotypes of the target individual. For example, the recommender system 340 may adjust the predicted value of the target phenotype based on other phenotypes of the target individual. The correlation between the target phenotype and other phenotypes may be retrieved from the phenotype relationship data 330 that analyzes the phenotype relationship as studied in science literature or other sources. For example, the correlation between target phenotype and other phenotypes may be determined from relationships between genotype data or genetic data in the literature, such as gene regulatory similarity, pathway similarity, or GWAS similarity. The recommender system 340 may also study the correlations of phenotypes based on its own data, such as data obtained from survey responses and analyze GWAS similarity based on its own data.

Figure 6B:
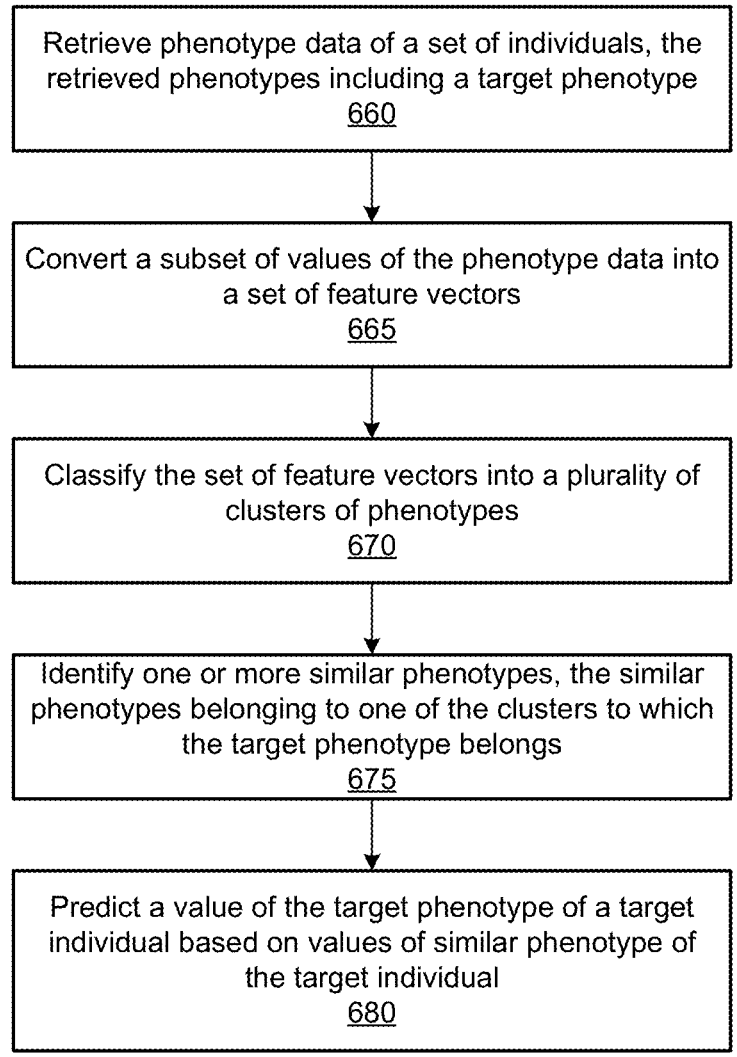
FIG. 6B is a flowchart depicting an example process of using a cluster-based recommender system predict a target phenotype based on correlated phenotypes, in accordance with an embodiment.

FIG. 6B illustrates a flowchart depicting an example process of predicting a target phenotype based on correlated phenotypes, in accordance with an embodiment. The recommender system 340 may retrieve 660 phenotype data of a set of individuals. The retrieved phenotypes include a target phenotype and other phenotypes. The recommender system 340 may convert 665 a subset of values of the phenotype data into a set of feature vectors. The values of the features may be generated based on the relationships as studied in scientific literature or based on own study of the recommender system 340. The recommender system 340 may classify 670 the set of feature vectors into a plurality of clusters of phenotypes. Each cluster may include one or more feature vectors that represent the corresponding phenotypes. The recommender system 340 may identify one or more similar phenotypes. The recommender system 340 may identify 675 one or more phenotypes that are similar to the target phenotype. Those phenotypes may be referred to as "similar phenotypes." The similar phenotypes belong to one of the clusters to which the target phenotype belongs. The recommender system 340 may predict 680 a value of the target phenotype of a target individual based on values of similar phenotype of the target individual. For example, based on the identified similar phenotypes, other individuals with known values of the target phenotype may be used to train a classifier, such as a regression model, a support vector machine, a neural network, to predict the target phenotype using the similar phenotypes.

The process illustrated in FIG. 6B may be used in conjunction with FIG. 6A in predicting or adjusting a phenotype value. In another embodiment, the process illustrated in FIG. 6B may be used independently to predict a target phenotype.

FIG. 7 is a chart showing an example study of correlations among different phenotypes, in accordance with an embodiment. The computing server 130 may present a series of survey questions that ask individuals to provide responses on their phenotypes that are related appearance traits, such as earlobes, earwax, eye color, freckling, hair color. Based on the responses, the computing server 130 performs a correlation study and the result is represented in a chart in FIG. 7. As shown in FIG. 7, among some of the phenotype included in the study, some of the phenotypes, such as skin pigmentation, skin sunburn, hair curl, hair color, and eye color are highly correlated. In predicting a phenotype of a target individual, if the undetermined phenotype is one of the phenotypes that is highly correlated to some other phenotypes, the computing server 130 may use the other phenotypes to predict the undetermined phenotype or may use this approach to further adjust a predicted value that is determined based on similar individuals.

The cluster-based approach may also be used to perform quality control of the survey responses. For example, besides predicting a phenotype or a survey response of a target individual, the recommender system 340 may treat survey responses of one or more other individuals as undetermined and use the cluster-based approach to generate predictions. Each of the individuals may be associated with her own set of similar individuals. In one case, the set of similar individuals and the individual may belong to the same cluster. The recommender system 340 may predict various survey responses of each individual based on survey responses of the set of individuals who are similar to that individual. The recommender system 340 may compare the predicted survey responses to actual survey responses to determine the reliability of the actual survey responses. In response to a survey question whose responses have the reliability that is lower than a threshold, the recommender system 340 may flag the survey question. The recommender system 340 may also adjust or remove the survey question from the system.

Example Hybrid Recommender System

Figure 8:
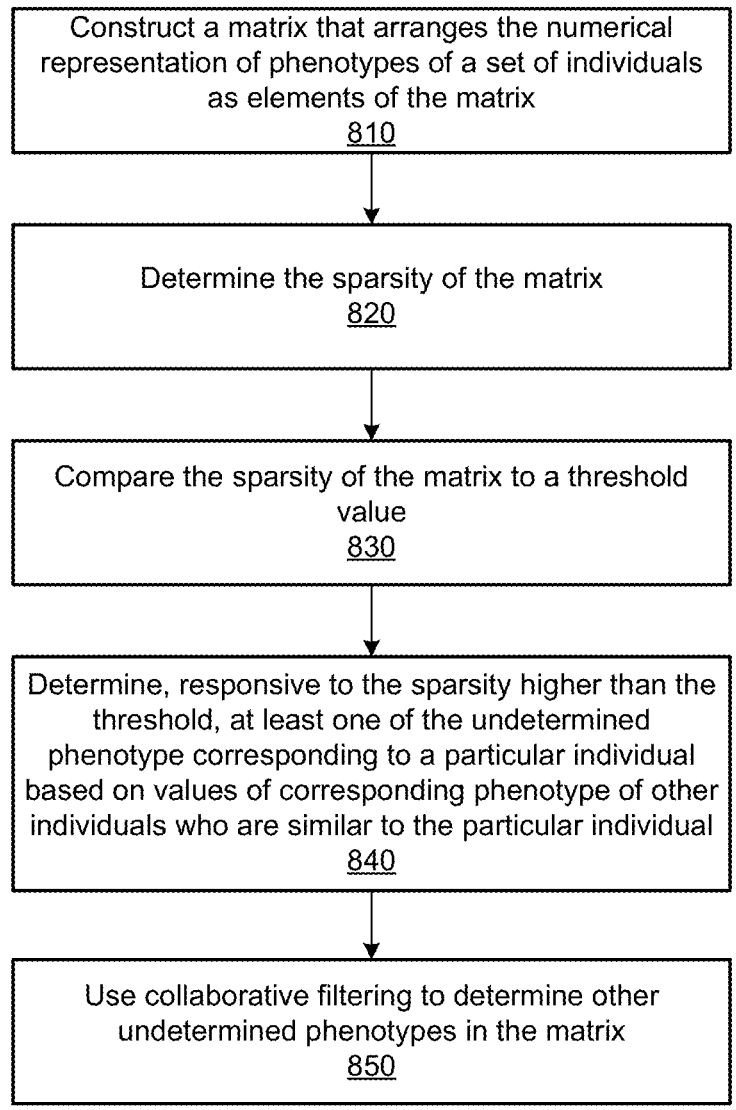
FIG. 8 is a flowchart depicting an example process of using a hybrid recommender system, in accordance with an embodiment.

The recommender system 340 may also be a hybrid system that uses both the cluster-based approach and matrix-based approach. FIG. 8 is a flowchart depicting an example process of using a hybrid recommender system, in accordance with an embodiment. A recommender system 340 may construct 810 a matrix that arranges the numerical representations of a set of individuals' phenotypes, survey responses, environmental factors, and/or other characteristics as elements of the matrix. The constructed matrix may be similar to the matrix 510 shown in FIG. 5.

In some cases, the constructed matrix may include too many undetermined values to prevent the recommender system 340 from directly using a matrix-based approach to accurately predict those undetermined values. The recommender system 340 may determine 820 the sparsity of the matrix by identifying a plurality of undetermined phenotypes (or survey responses) that represent the sparsity of the matrix. The sparsity of the matrix may correspond to the number of undetermined values (e.g., number of undetermined phenotype values) in the matrix among the set of individuals. If the sparsity is too high, the recommender system 340 may use the cluster-based approach to fill in some of the undetermined values before collaborative filtering, such as the matrix-based approach, is applied. The recommender system 340 may compare 830 the sparsity of the matrix to a threshold value.

The threshold value may be determined based on the matrix. In one embodiment, the recommender system 340 may determine a level of sparsity that will result in the failure of collaborative filtering, whether it is a matrix-based approach or other collaborative filtering approach such as cluster-based collaborative filtering. For example, the recommender system 340 may treat a subset of known values in the matrix as undetermined values. The recommender system 340 runs collaborative filtering to predict the subset of known values and compares the predictions to the actual values to determine the performance of collaborative filtering. If the result of the collaborative filtering (e.g., the matrix-based approach or another approach) is satisfactory, the recommender system 340 may expand the subset of known values that are treated as undetermined values to increase the sparsity of the matrix (e.g., 10% sparsity in the first round, 20% in the second round) and repeat the matrix-based approach. The result of the collaborative filtering is analyzed against the actual values. The process to increase the sparsity of the matrix may be repeated continuously to determine a threshold at which collaborative filtering no longer produces a satisfactory result.

In response to the sparsity of the matrix being higher than the threshold, the recommender system 340 may determine 840 at least one of the undetermined value (e.g. an undetermined phenotype value) corresponding to a particular individual using the cluster-based approach. For example, the undermined phenotype values of the particular individual may be determined based on values of the corresponding phenotype of other individuals who are similar to the particular individual. The particular individual does not have to be the target individual. The particular individual can be any individual in the matrix who has one or more undetermined value. The use of the cluster-based approach may be repeated for one or more individuals who have undetermined values in the matrix. The process reduces the sparsity of the matrix. In turn, the recommender system 340 may use 850 collaborative filtering to determine other undetermined phenotypes in the matrix.

Using the hybrid approach, the recommender system 340 may determine predictions of a first subset of the undetermined survey responses based on the plurality of the clusters that are identified in the cluster-based approach. Each undetermined survey response in the first subset of a particular individual may be determined based on survey responses of similar individuals such as individuals who belong to the same cluster as the particular individual. The recommender system 340 may determine predictions of a second subset of the undetermined survey responses based on collaborative filtering.

Example Experimental Results

Figure 9:
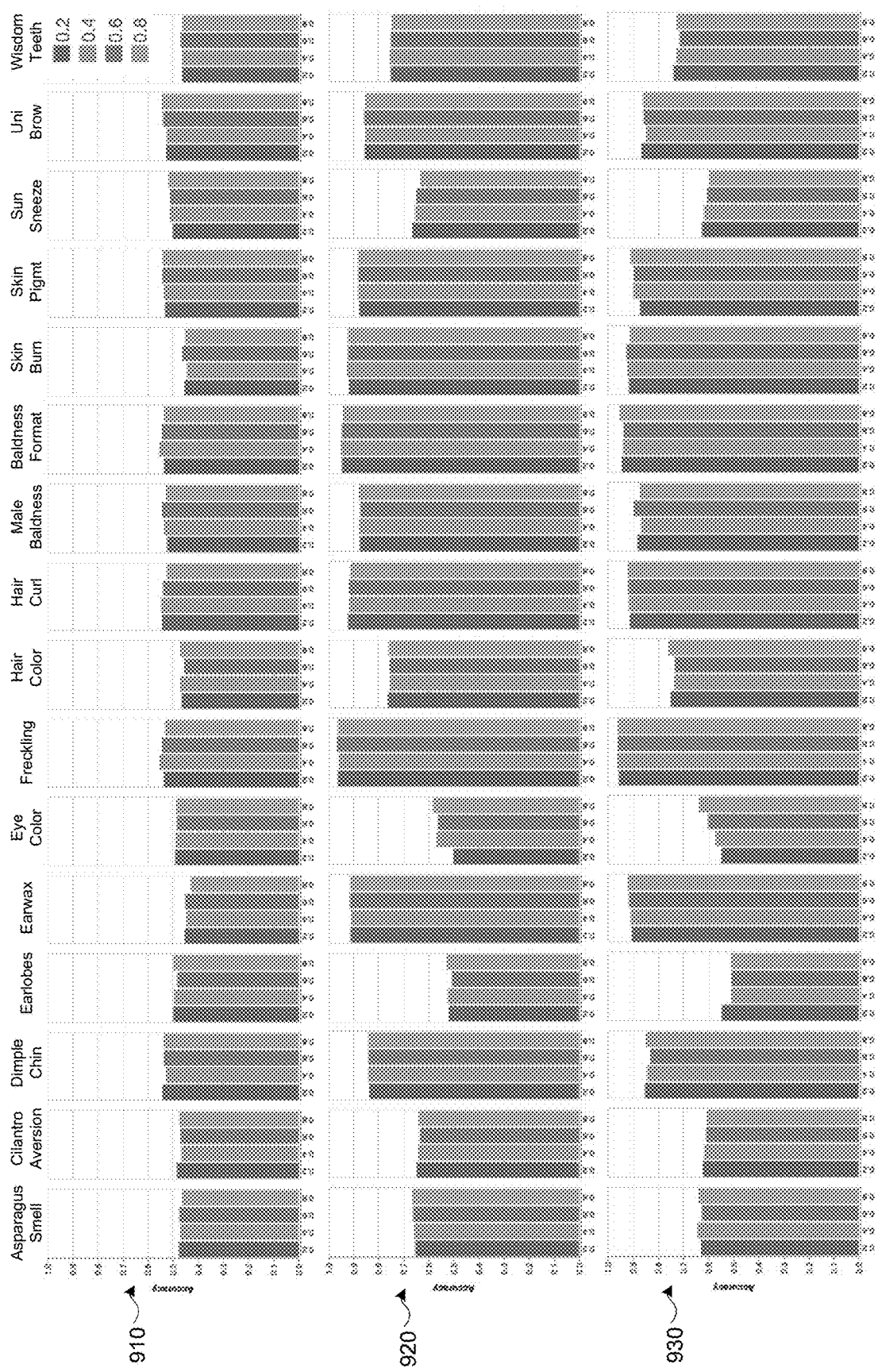
FIG. 9 shows multiple charts that illustrate the effectiveness of using recommender systems to predict phenotypes, in accordance with an embodiment.

FIG. 9 shows multiple charts that illustrate the effectiveness of using recommender systems to predict phenotypes, in accordance with an embodiment. In a study, a portion of survey data (e.g., 20%, 40%, 60%, and 80%) is randomly hidden. A recommender system is used to predict the phenotypes of the hidden data using the non-hidden portion of the data, which are survey responses by similar individuals. Each phenotype is associated with binary possible outcomes, which are the presence of the phenotype and the absence of the phenotype. The top chart 910 shows the result of a random predictor, which predicts the outcome randomly. The result of the random predictor serves as a baseline comparison of the recommender systems. The middle chart 920 shows the results of the accuracy of predictions using a matrix-based collaborative filtering recommender system. The bottom chart 930 shows the results of the accuracy of predictions using a cluster-based recommender system. The results show that both recommender systems accurately predict the values of majority of phenotypes. The results also show that some of the phenotypes are more accurately predicted using recommender systems while some phenotypes, such as asparagus smell in urine and earlobes are less accurately predicted using a recommender system. The variances in the results may be explained due to skewness in the prevalence of some of the phenotypes and noise responses.

Computing Machine Architecture

Figure 10:
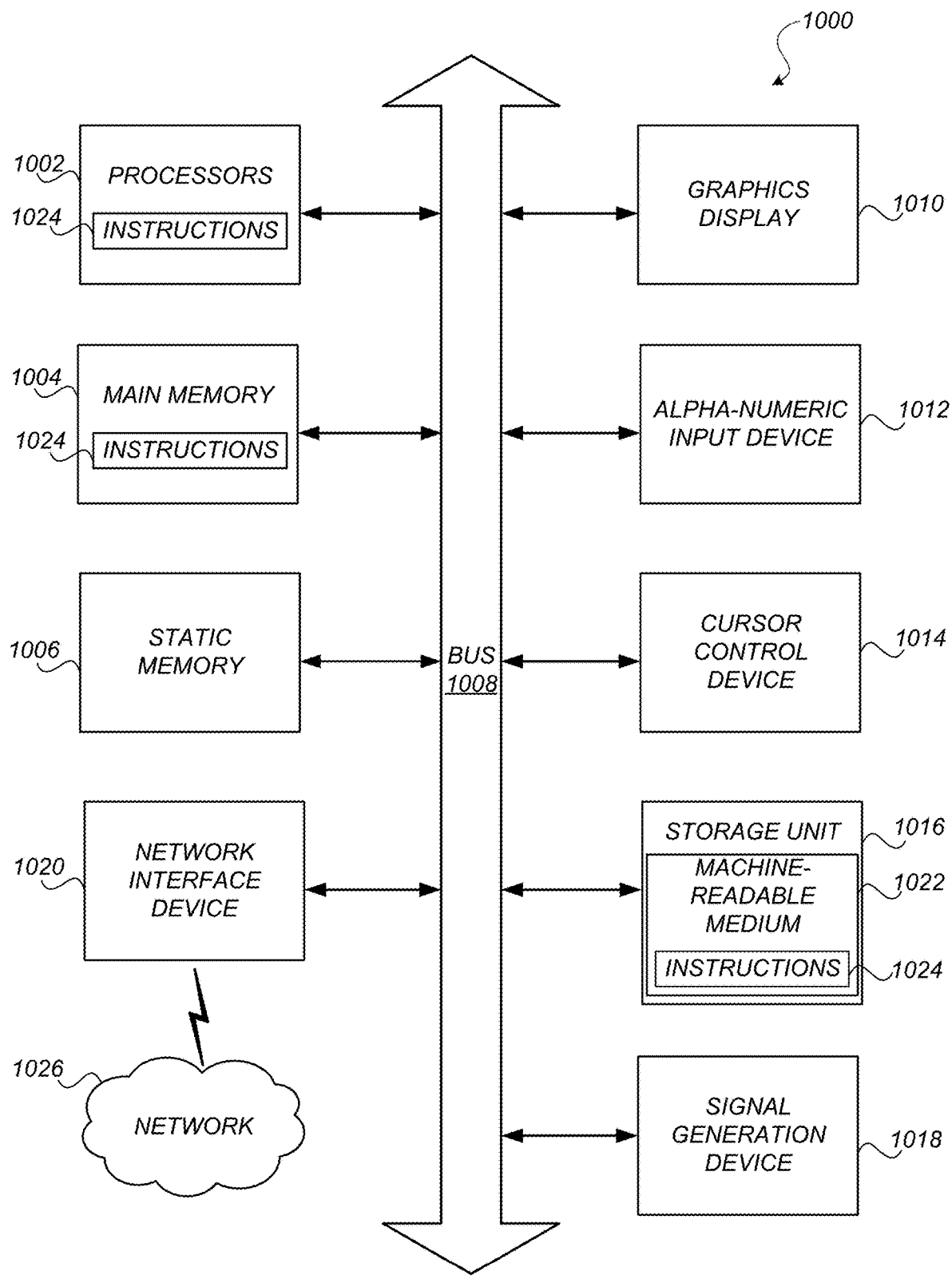
FIG. 10 is a block diagram of an example computing device, in accordance with an embodiment.

FIG. 10 is a block diagram illustrating components of an example computing machine that is capable of reading instructions from a computer-readable medium and execute them in a processor (or controller). A computer described herein may include a single computing machine shown in FIG. 10, a virtual machine, a distributed computing system that includes multiples nodes of computing machines shown in FIG. 10, or any other suitable arrangement of computing devices.

By way of example, FIG. 10 shows a diagrammatic representation of a computing machine in the example form of a computer system 1000 within which instructions 1024 (e.g., software, program code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 10 may correspond to any software, hardware, or combined components shown in FIGS. 1 and 2, including but not limited to, the client device 110, the computing server 130, recommender system 340, and various engines, interfaces, terminals, and machines shown in FIG. 2. While FIG. 10 shows various hardware and software elements, each of the components described in FIGS. 1 and 2 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1024 that specify actions to be taken by that machine. Further, while only a single machine is illustrated, the term "machine" and "computer" may also be taken to include any collection of machines that individually or jointly execute instructions 1024 to perform any one or more of the methodologies discussed herein.

The example computer system 1000 includes one or more processors 1002 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 1000 may also include a storage medium such as a memory 1004 that store computer code including instructions 1024 that may cause the processors 1002 to perform certain actions when the instructions are executed, directly or indirectly by the processors 1002. Instructions can be any directions, commands, or orders that may be stored in different forms, such as equipment-readable instructions, programming instructions including source code, and other communication signals and orders. Instructions may be used in a general sense and are not limited to machine-readable codes.

One and more methods described herein improve the operation speed of the processors 1002 and reduces the space required for the memory 1004. For example, the machine learning methods described herein reduces the complexity of the computation of the processors 1002 by applying one or more novel techniques that simplify the steps in training, reaching convergence, and generating results of the processors 1002. The algorithms described herein also reduces the size of the models and datasets to reduce the storage space requirement for memory 1004.

The performance of certain of the operations may be distributed among the more than processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Even though in the specification or the claims may refer some processes to be performed by a processor, this should be construed to include a joint operation of multiple distributed processors.

The computer system 1000 may include a main memory 1004, and a static memory 1006, which are configured to communicate with each other via a bus 1008. The computer system 1000 may further include a graphics display unit 1010 (e.g., a plasma display panel (PDP), a liquid crystal display (LCD), a projector, or a cathode ray tube (CRT)). The graphics display unit 1010, controlled by the processors 1002, displays a graphical user interface (GUI) to display one or more results and data generated by the processes described herein. The computer system 1000 may also include alphanumeric input device 1012 (e.g., a keyboard), a cursor control device 1014 (e.g., a mouse, a trackball, a joystick, a motion sensor, or other pointing instrument), a storage unit 1016 (a hard drive, a solid-state drive, a hybrid drive, a memory disk, etc.), a signal generation device 1018 (e.g., a speaker), and a network interface device 1020, which also are configured to communicate via the bus 1008.

The storage unit 1016 includes a computer-readable medium 1022 on which is stored instructions 1024 embodying any one or more of the methodologies or functions described herein. The instructions 1024 may also reside, completely or at least partially, within the main memory 1004 or within the processor 1002 (e.g., within a processor's cache memory) during execution thereof by the computer system 1000, the main memory 1004 and the processor 1002 also constituting computer-readable media. The instructions 1024 may be transmitted or received over a network 1026 via the network interface device 1020.

While computer-readable medium 1022 is shown in an example embodiment to be a single medium, the term "computer-readable medium" should be taken to include a single medium or multiple media (e.g., a centralized or distributed database, or associated caches and servers) able to store instructions (e.g., instructions 1024). The computer-readable medium may include any medium that is capable of storing instructions (e.g., instructions 1024) for execution by the processors (e.g., processors 1002) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Embodiments according to the invention are in particular disclosed in the attached claims directed to a method and a computer program product, wherein any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter which can be claimed comprises not only the combinations of features as set out in the disclosed embodiments but also any other combination of features from different embodiments. Various features mentioned in the different embodiments can be combined with explicit mentioning of such combination or arrangement in an example embodiment. Furthermore, any of the embodiments and features described or depicted herein can be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The following applications are incorporated by reference in their entirety for all purposes: (1) U.S. patent application Ser. No. 15/591,099, entitled "Haplotype Phasing Models," filed on Oct. 19, 2015, (2) U.S. patent application Ser. No. 15/168,011, entitled "Discovering Population Structure from Patterns of Identity-By-Descent," filed on May 28, 2016, (3) U.S. "Reducing Error in Predicted Genetic Relationships," filed on Apr. 13, 2017, (4) U.S. patent application Ser. No. 15/209,458, entitled "Local Genetic Ethnicity Determination System," filed on Jul. 13, 2016, and (5) U.S. patent application Ser. No. 14/029,765, entitled "Identifying Ancestral Relationships Using a Continuous stream of Input," filed on Sep. 17, 2013.

What is claimed is:

1. A computer-implemented method, comprising:
retrieving survey responses of a set of individuals regarding a set of phenotypes of the individuals, the set of individuals comprising a target individual;
constructing a matrix that arranges the set of individuals in a first dimension of the matrix and the set of phenotypes in a second dimension of the matrix, at least a subset of elements in the matrix being numerical representations of the individuals' phenotypes obtained from the survey responses;
identifying one or more undetermined phenotypes of the target individual, the matrix having no value at particular elements corresponding to the one or more undetermined phenotypes of the target individual;
determining a sparsity of the matrix, the sparsity of the matrix corresponding to a number of undetermined values in the matrix;
determining, responsive to the sparsity higher than a threshold, at least one of the undetermined values corresponding to a particular individual based on corresponding values of other individuals who are similar to the particular individual to reduce the sparsity of the matrix; and
determining a prediction of the one or more undetermined phenotypes of the target individual by performing collaborative filtering using a machine learning technique, the collaborative filtering based on other phenotypes of the target individual and based on at least another individual's phenotypes as represented in numerical representations in the matrix, performing the collaborative filtering using the machine learning technique comprises:
performing a factorization of the matrix to estimate two or more lower dimensionality matrices that generates an approximation of the matrix, and
using coordinate descent to iteratively adjust values in elements of the two or more lower dimensionality matrices to reduce differences between the approximation and the matrix.

2. The computer-implemented method of claim 1, wherein the survey responses comprising responses to one or more survey questions, the survey questions comprising one or more of the following: an appearance trait question, a social-economical question, a cultural question, a preference question, a geographical question, a health-related question, or a family health history question.

3. The computer-implemented method of claim 1, wherein the matrix further comprises additional elements related to environmental factors of the set of individuals.

4. The computer-implemented method of claim 1, wherein
the lower dimensionality matrices comprising values related to a set of latent factors; and performing the collaborative filtering using the machine learning technique further comprises:

determining the prediction based on a set of values of the latent factors corresponding to the target individual.

5. The computer-implemented method of claim 4, wherein a first lower dimensionality matrix arranges the set of individuals in a first dimension of the first lower dimensionality matrix and the set of latent factors in a second dimension of the first lower dimensionality matrix; and
wherein a second lower dimensionality matrix arranges the set of latent factors in a first dimension of the second lower dimensionality matrix and the set of phenotypes in a second dimension of the second lower dimensionality matrix.

6. The computer-implemented method of claim 1, further comprising:
predicting the survey responses of one or more other individuals using the collaborative filtering; and
comparing the predicted survey responses to actual survey responses of the other individuals to determine reliability of the actual survey responses.

7. The computer-implemented method of claim 6, further comprising:
identifying one or more survey questions whose responses having the reliability that is lower than a threshold; and
adjusting or removing the one or more survey questions.

8. The computer-implemented method of claim 1, further comprising:
sending the prediction of the undetermined phenotype of the target individual to be presented at a graphical user interface that displays a profile of the target individual.

9. The computer-implemented method of claim 1, wherein the other individuals who are similar to the particular individual are identified based on a length of identity-by-descent (IBD) segments shared between the particular individual and each of the other individuals.

10. The computer-implemented method of claim 1, wherein the other individuals who are similar to the particular individual are identified by:
retrieving genetic data of the particular individual and a set of candidate individuals;
representing the genetic data of the particular individual and the set of candidate individuals as a plurality of feature vectors;
clustering the plurality of feature vectors to identify a particular cluster to which the feature vector that corresponds to the particular individual belongs; and
identifying a subset of candidate individuals corresponding to other feature vectors in the particular cluster as the similar individuals.

11. The computer-implemented method of claim 1, wherein the other individuals who are similar to the particular individual are identified based on pedigree data between the particular individual and each of the other individuals.

12. A non-transitory computer readable medium configured to store instructions, the instructions, when executed by one or more processors, cause the one or more processors to perform steps comprising:
retrieving survey responses of a set of individuals regarding a set of phenotypes of the individuals, the set of individuals comprising a target individual;
constructing a matrix that arranges the set of individuals in a first dimension of the matrix and the set of phenotypes in a second dimension of the matrix, at least a subset of elements in the matrix being numerical representations of the individuals' phenotypes obtained from the survey responses;
identifying one or more undetermined phenotypes of the target individual, the matrix having no value at particular elements corresponding to the one or more undetermined phenotypes of the target individual;
determining a sparsity of the matrix, the sparsity of the matrix corresponding to a number of undetermined values in the matrix;
determining, responsive to the sparsity higher than a threshold, at least one of the undetermined values corresponding to a particular individual based on corresponding values of other individuals who are similar to the particular individual to reduce the sparsity of the matrix; and
determining a prediction of the one or more undetermined phenotypes of the target individual by performing collaborative filtering using a machine learning technique, the collaborative filtering based on other phenotypes of the target individual and based on at least another individual's phenotypes as represented in numerical representations in the matrix, performing the collaborative filtering using the machine learning technique comprises:
performing a factorization of the matrix to estimate two or more lower dimensionality matrices that generates an approximation of the matrix, and
using coordinate descent to iteratively adjust values in elements of the two or more lower dimensionality matrices to reduce differences between the approximation and the matrix.

13. The non-transitory computer readable medium of claim 12, wherein the steps further comprise:
predicting the survey responses of one or more other individuals using the collaborative filtering; and
comparing the predicted survey responses to actual survey responses of the other individuals to determine reliability of the actual survey responses.

14. The non-transitory computer readable medium of claim 13, wherein the steps further comprise:
identifying one or more survey questions whose responses having the reliability that is lower than a threshold; and
adjusting or removing the one or more survey questions.

15. The non-transitory computer readable medium of claim 12, wherein the steps further comprise:
sending the prediction of the undetermined phenotype of the target individual to be presented at a graphical user interface that displays a profile of the target individual.

16. A system comprising:
one or more processors;
a storage medium configured to store instructions, the instructions, when executed by the one or more processors, cause the one or more processors to perform steps comprising:
retrieving survey responses of a set of individuals regarding a set of phenotypes of the individuals, the set of individuals comprising a target individual;
constructing a matrix that arranges the set of individuals in a first dimension of the matrix and the set of phenotypes in a second dimension of the matrix, at least a subset of elements in the matrix being numerical representations of the individuals' phenotypes obtained from the survey responses;
identifying one or more undetermined phenotypes of the target individual, the matrix having no value at particular elements corresponding to the one or more undetermined phenotypes of the target individual;

determining a sparsity of the matrix, the sparsity of the matrix corresponding to a number of undetermined values in the matrix;

determining, responsive to the sparsity higher than a threshold, at least one of the undetermined values corresponding to a particular individual based on corresponding values of other individuals who are similar to the particular individual to reduce the sparsity of the matrix; and determining a prediction of the one or more undetermined phenotypes of the target individual by performing collaborative filtering using a machine learning technique, the collaborative filtering based on other phenotypes of the target individual and based on at least another individual's phenotypes as represented in numerical representations in the matrix, performing the collaborative filtering using the machine learning technique comprises:

performing a factorization of the matrix to estimate two or more lower dimensionality matrices that generates an approximation of the matrix, and using coordinate descent to iteratively adjust values in elements of the two or more lower dimensionality matrices to reduce differences between the approximation and the matrix.

17. The system of claim 16, wherein the steps further comprise:

predicting the survey responses of one or more other individuals using the collaborative filtering; and comparing the predicted survey responses to actual survey responses of the other individuals to determine reliability of the actual survey responses.

18. The system of claim 17, wherein the steps further comprise:

identifying one or more survey questions whose responses having the reliability that is lower than a threshold; and adjusting or removing the one or more survey questions.

19. The system of claim 16, wherein the steps further comprise:

sending the prediction of the undetermined phenotype of the target individual to be presented at a graphical user interface that displays a profile of the target individual.

\* \* \* \* \*